(12) United States Patent
Malamas et al.

(10) Patent No.: US 7,456,186 B2
(45) Date of Patent: Nov. 25, 2008

(54) DIPHENYLIMIDAZOPYRIMIDINES AS INHIBITORS OF β-SECRETASE

(75) Inventors: Michael S. Malamas, Jamison, PA (US); James J. Erdei, Philadelphia, PA (US); Iwan S. Gunawan, Somerset, NJ (US); Keith Douglas Barnes, Rexford, NY (US); Matthew Robert Johnson, Guilderland, NY (US); Yu Hui, New London, CT (US)

(73) Assignee: Wyeth, Madison, NJ (US)

( * ) Notice: Subject to any disclaimer, the term of this patent is extended or adjusted under 35 U.S.C. 154(b) by 53 days.

(21) Appl. No.: 11/152,925

(22) Filed: Jun. 15, 2005

(65) Prior Publication Data
US 2005/0282826 A1  Dec. 22, 2005

Related U.S. Application Data

(60) Provisional application No. 60/580,187, filed on Jun. 16, 2004.

(51) Int. Cl.
*A61K 31/519* (2006.01)
*C07D 487/04* (2006.01)
*A61P 25/26* (2006.01)

(52) U.S. Cl. .............. 514/259.1; 544/281; 544/230

(58) Field of Classification Search .............. 544/281, 544/230; 514/259.1
See application file for complete search history.

(56) References Cited

U.S. PATENT DOCUMENTS

| | | | |
|---|---|---|---|
| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2006/0111370 | A1 | 5/2006 | Zhu et al. |
| 2006/0160828 | A1 | 7/2006 | Malamas et al. |
| 2006/0173049 | A1 | 8/2006 | Malamas et al. |
| 2006/0183790 | A1 | 8/2006 | Cole et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2007/0203116 | A1 | 8/2007 | Quagliato et al. |
| 2008/0051390 | A1 | 2/2008 | Malamas et al. |

FOREIGN PATENT DOCUMENTS

| EP | 0861831 A1 | 9/1998 |
|---|---|---|
| GB | 2013192 A | 8/1979 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

Abbott e tal., Molecular Medicine Today, 1996, vol. 2, p. 106-113.
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and charaterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006, vol. 14, pp. 561-573.
Alzheimer's Disease, retrieved from internet on Jun. 27, 2007, http://www.mayoclinic.com/health/alzheimers-disease/DA00161/DSECTION-3.
National Institute of Neurological Disorders and Stroke, "Alzheimer's Disease Information Page", retrieved from internet on Jun. 27, 2007, http://www.ninds.nih.gov/disorders/alzheimersdisease/alzheimersdisease.htm.

(Continued)

*Primary Examiner*—Brenda L. Coleman
*Assistant Examiner*—Susanna Moore
(74) *Attorney, Agent, or Firm*—Joel Silver; Scott Larsen; Andrea Dorigo

(57) ABSTRACT

The present invention provides a compound of formula I and the use thereof for the therapeutic treatment, prevention or amelioration of a disease or disorder characterized by elevated β-amyloid deposits or β-amyloid levels in a patient.

(I)

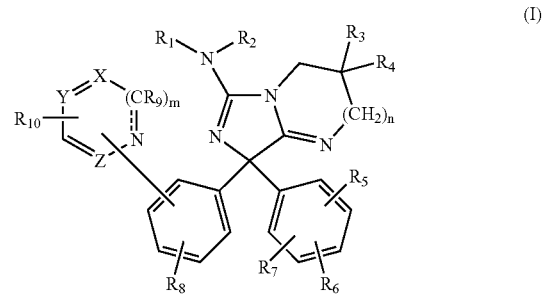

17 Claims, No Drawings

OTHER PUBLICATIONS

PCT Preliminary Report on Patentability, Written Opinion of the ISR, International Patent Application PCT/US2006/024793, International filing date Jun. 26, 2006.

PCT Preliminary Report on Patentability, Written Opinion of the ISR, International Patent Application PCT/US2006/024912, International filing date Jun. 26, 2006.

Selkoe, "Alzheimer's Disease: Genes, Proteins, and Therapy", Physiological Reviews, 2001, vol. 81(2), pp. 741-766.

Su et al., "Drug delivery across the blood-brain barrier: why is it difficult? How to measure and improve it?", Expert Opinion on Drug Delivery, Abstract, 2006, vol. 3, pp. 419-425.

Tao et al., "Synthesis of Conformationally constrained spirohydantoins with a Dibenzo[a,d]heptadiene ring", Synthesis 2000, No. 10, pp. 1449-1453.

Vandana et al., "Transferring coupled liposomes as drug delivery carriers for brain trageting of 5-florouracil", Journal of Drug Targeting, Abstract, 2005, vol. 13 pp. 245-250.

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.

Yamada et al., "Hydantoin derivatives, I. Actions on central nervous system of 5,5-diarylhydantoins and 5,5-diarylhydantion-2-imines", Abstract, Oyo Yakuri, 1975, vol. 9(6), pp. 841-847.

DIPHENYLIMIDAZOPYRIMIDINES AS INHIBITORS OF β-SECRETASE

This application claims the benefit under 35 U.S.C. §119 (e) to U.S. provisional application No. 60/580,187, filed Jun. 16, 2004, which is hereby incorporated by reference in its entirety.

BACKGROUND OF THE INVENTION

Alzheimer's disease (AD), a progressive degenerative disease of the brain primarily associated with aging, is a serious healthcare problem. Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years. Patients with AD display characteristic β-amyloid deposits in the brain and in cerebral blood vessels (β-amyloid angiopathy) as well as neurofibrillary tangles. Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other dementia-inducing disorders.

The family of proteins known as β-amyloid are thought to be causal for the pathology and subsequent cognitive decline in Alzheimer's disease. Proteolytic processing of the amyloid precursor protein (APP) generates amyloid β (A-beta) peptide; specifically, A-beta is produced by the cleavage of APP at the N-terminus by β-secretase and at the C-terminus by one or more γ-secretases. Aspartyl protease enzyme, or β-secretase enzyme (BACE), activity is correlated directly to the generation of A-beta peptide from APP (Sin ha, et al, *Nature*, 1999, 402, 537-540). Increasingly, studies indicate that the inhibition of the β-secretase enzyme, inhibits the production of A-beta peptide. The inhibition of β-secretase and consequent lowering of A-beta peptide may lead to the reduction of β-amyloid deposits in the brain and β-amyloid levels in the cerebral blood vessels and to an effective treatment of a disease or disorder caused thereby.

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

The present invention provides a diphenylimidazopyrimidine or -imidazole amine of formula I

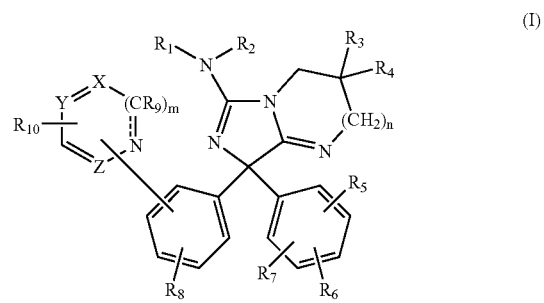

wherein X is N, NO or $CR_{19}$;
Y is N, NO or $CR_{11}$;
Z is N, NO or $CR_{20}$ with the proviso that no more than two of X, Y or Z may be N or NO;
$R_1$ and $R_2$ are each independently H, CN or an optionally substituted $C_1$-$C_4$alkyl group;
$R_3$ and $R_4$ are each independently H, or an optionally substituted $C_1$-$C_4$ alkyl group or $R_3$ and $R_4$ may be taken together to form a 3- to 7-membered ring optionally containing one or two heteroatoms selected from O, N or S or $R_3$ may be taken together with the atom to which it is attached and an adjacent carbon atom to form a double bond;
$R_5$ and $R_6$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_5$ and $R_6$ may be taken together with the atoms to which they are attached to form an optionally substituted 5- to 7-membered ring optionally containing one or two heteroatoms selected from O, N or S;
$R_7$, $R_8$, $R_9$, $R_{10}$, $R_{11}$, $R_{19}$ and $R_{20}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
m is 0 or 1;
n is 0, 1, 2 or 3;
===== is a single bond or a double bond with the proviso that when m is 0 then ===== must be a single bond;
$R_{12}$, $R_{13}$ and $R_{16}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and
$R_{14}$, $R_{15}$, $R_{17}$ and $R_{18}$ are each independently H or $C_1$-$C_4$alkyl; or a tautomer thereof, a stereoisomer thereof or a pharmaceutically acceptable salt thereof.

The present invention also provides therapeutic methods and pharmaceutical compositions useful for the treatment, prevention or amelioration of a disease or disorder characterized by increased β-amyloid deposits or increased β-amyloid levels in a patient.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deteoriation and death. The exact cause of AD is unknown, but increasing evidence indicates that amyloid beta peptide (A-beta) plays a central role in the pathogenesis of the disease. (D. B. Schenk; R. E. Rydel et al., Journal of Medicinal Chemistry, 1995, 21, 4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenreative and dementia-inducing disorders. Over expression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Parallel to BACE1, a second homologous aspartyl protease named BACE2 was found to have β-secretase activity in vitro. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that diphenylimidazopyrimidine amine or diphenylimidazoimidazole amine compounds of formula I demonstrate inhibition of β-secretase and the selective inhibition of BACE1. Advantageously, said pyrimidinamine or imidazolamine compounds may be used as effective therapeutic agents for the treatment, prevention or amelioration of a disease or disorder characterized by elevated β-amyloid deposits or β-amyloid levels in a patient. Accordingly, the present invention provides an imidazopyrimidine or imidazoimidazole amine compound of formula I

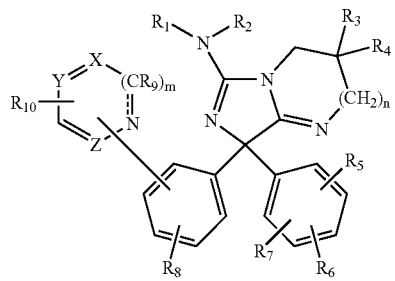

(I)

wherein X is N, NO or $CR_{19}$;

Y is N, NO or $CR_{11}$;

Z is N, NO or $CR_{20}$ with the proviso that no more than two of X, Y or Z may be N or NO;

$R_1$ and $R_2$ are each independently H, CN or an optionally substituted $C_1$-$C_4$alkyl group;

$R_3$ and $R_4$ are each independently H, or an optionally substituted $C_1$-$C_4$ alkyl group or $R_3$ and $R_4$ may be taken together to form a 3- to 7-membered ring optionally containing one or two heteroatoms selected from O, N or S or $R_3$ may be taken together with the atom to which it is attached and an adjacent carbon atom to form a double bond;

$R_5$ and $R_6$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_5$ and $R_6$ may be taken together with the atoms to which they are attached to form an optionally substituted 5- to 7-membered ring optionally containing one or two heteroatoms selected from O, N or S;

$R_7$, $R_8$, $R_9$, $R_{10}$, $R_{11}$, $R_{19}$ and $R_{20}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

m is 0 or 1;

n is 0, 1, 2 or 3;

⁓⁓⁓ is a single bond or a double bond with the proviso that when m is 0 then ⁓⁓⁓ must be a single bond;

$R_{12}$, $R_{13}$ and $R_{16}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and $R_{14}$, $R_{15}$, $R_{17}$ and $R_{18}$ are each independently H or $C_1$-$C_4$alkyl; or a tautomer thereof, a stereoisomer thereof or a pharmaceutically acceptable salt thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein $X_1$ is NR, O or S; and R is H or an optional substituent as described hereinbelow:

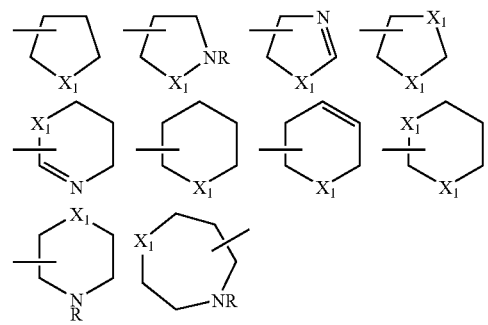

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term aryl ($C_1$-$C_4$)alkyl designates an aryl group as defined hereinabove attached to a $C_1$-$C_4$alkyl group which may be straight or branched. Said aryl($C_1$-$C_4$)alkyl groups include benzyl, phenethyl, napthtylmethyl, or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different. Preferably the term haloalkyl designates $CF_3$ and the term haloalkoxy designates $OCF_3$.

In the specification and claims, when the terms $C_1$-$C_6$alkyl, $C_2$-$C_6$alkenyl, $C_2$-$C_6$alkynyl, $C_3$-$C_8$cycloalkyl, cycloheteroalkyl, aryl, aryl($C_1$-$C_4$)alkyl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more tautomers. One skilled in the art will recognize that compounds of formula I may also exist as the tautomer It as shown below.

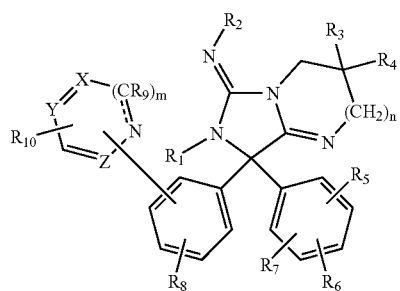

(It)

Tautomers often exist in equilibrium with each other. As these tautomers interconvert under environmental and physiological conditions, they provide the same useful biological effects. The present invention includes mixtures of such tautomers as well as the individual tautomers of Formula I and Formula It.

The compounds of the invention may contain one or more asymmetric carbon atoms or one or more asymmetric (chiral) centers and may thus give rise to optical isomers and diastereomers. Thus, the invention includes such optical isomers and disastereomers; as well as the racemic and resolved, enantiomerically pure stereoisomers; as well as other mixtures of the R and S stereoisomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof, the tautomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein $R_1$ and $R_2$ are H. Another group of preferred compounds of the invention are those compounds of formula I wherein m and n are 1. Also preferred are those formula I compounds wherein X is N. A further group of preferred compounds of the invention are those compounds of formula I wherein the nitrogen-containing 5-membered or 6-membered heteroaryl ring is attached to the phenyl ring in the 3-position of the phenyl ring; this preferred group of formula I compounds is designated in the specification and claims as formula Ia. The formula Ia compound is shown below.

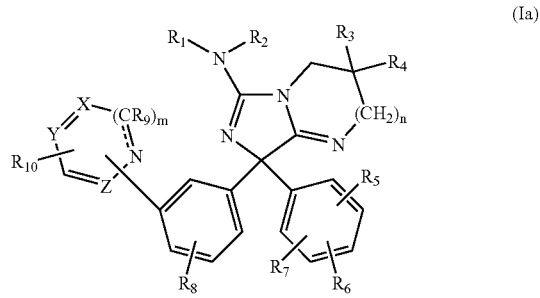

(Ia)

More preferred compounds of the invention are those compounds of formula Ia wherein the nitrogen-containing heteroaryl ring is a 6-membered ring and is attached to the phenyl ring in the 3-position of said heteroaryl ring; this more preferred group of formula I compounds is designated in the specification and claims as formula Ib. Formula Ib is shown below.

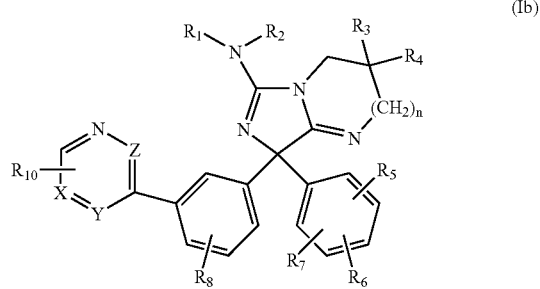

(Ib)

Another group of more preferred compounds of the invention are those compounds of formula Ib wherein $R_1$ and $R_2$ are H.

A further group of more preferred compounds of the invention are those compounds of formula Ib wherein Y is $CR_{11}$ and $R_1$ and $R_2$ are H.

Examples of preferred compounds of formula I include:
8-(3-pyrimidin-5-ylphenyl)-8-[4-(trifluoromethoxy)phenyl]-2,3,4,8-tetrahydroimidazo[1,5-a]pyrimidin-6-amine;
7-(3-pyrimidin-5-ylphenyl)-7-[4-(trifluoromethoxy)phenyl]-7H-imidazo[1,5-a]imidazol-5-amine;
8-[4-fluoro-3-(4-fluoropyridin-3-yl)phenyl]-8-[4-(trifluoromethoxy)phenyl]-2,3,4,8-tetrahydroimidazo[1,5-a]pyrimidin-6-amine;
8-[3-(5-fluoropyridin-3-yl)phenyl]-8-[4-(trifluoromethoxy)phenyl]-2,3,4,8-tetrahydroimidazo[1,5-a]pyrimidin-6-amine;
8-[3-(5-chloropyridin-3-yl)phenyl]-8-[4-(trifluoromethoxy)phenyl]-2,3,4,8-tetrahydroimidazo[1,5-a]pyrimidin-6-amine;
(8S)-8-[3-(2-fluoropyridin-3-yl)phenyl]-8-[4-(trifluoromethoxy)phenyl]-2,3,4,8-tetrahydroimidazo[1,5-a]pyrimidin-6-amine;
(8R)-8-[3-(2-fluoropyridin-3-yl)phenyl]-8-[4-(trifluoromethoxy)phenyl]-2,3,4,8-tetrahydroimidazo[1,5-a]pyrimidin-6-amine;
(8R)-8-(3-pyrimidin-5-ylphenyl)-8-[4-(trifluoromethoxy)phenyl]-2,3,4,8-tetrahydroimidazo[1,5-a]pyrimidin-6-amine;
(8S)-8-(3-pyrimidin-5-ylphenyl)-8-[4-(trifluoromethoxy)phenyl]-2,3,4,8-tetrahydroimidazo[1,5-a]pyrimidin-6-amine;
8-[3-(4-fluoropyridin-3-yl)phenyl]-8-[4-(trifluoromethoxy)phenyl]-2,3,4,8-tetrahydroimidazo[1,5-a]pyrimidin-6-amine;
8-[3-(2-fluoropyridin-3-yl)phenyl]-8-[4-methoxyphenyl]-2,3,4,8-tetrahydroimidazo[1,5-a]pyrimidin-6-amine;
8-(4-methoxyphenyl)-8-(3-pyrimidin-5-ylphenyl)-2,3,4,8-tetrahydroimidazo[1,5-a]pyrimidin-6-amine;
8-(4-fluoro-3-pyrimidin-5-ylphenyl)-8-(4-methoxyphenyl)-2,3,4,8-tetrahydroimidazo[1,5-a]pyrimidin-6-amine;
8-[4-fluoro-3-(2-fluoropyridin-3-yl)phenyl]-8-(4-methoxyphenyl)-2,3,4,8-tetrahydroimidazo[1,5-a]pyrimidin-6-amine;
8-(4-fluoro-3-pyrimidin-5-ylphenyl)-8-[4-(trifluoromethoxy)phenyl]-2,3,4,8-tetrahydroimidazo[1,5-a]pyrimidin-6-amine;
8-[3-(2-fluoropyridin-3-yl)phenyl]-8-[4-(trifluoromethoxy)phenyl]-2,3,4,8-tetrahydroimidazo[1,5-a]pyrimidin-6-amine;
8-[4-fluoro-3-(5-fluoropyridin-3-yl)phenyl]-8-[4-(trifluoromethoxy)phenyl]-2,3,4,8-tetrahydroimidazo[1,5-a]pyrimidin-6-amine;
8-[4-fluoro-3-(2-fluoropyridin-3-yl)phenyl]-8-[4-(trifluoromethoxy)phenyl]-2,3,4,8-tetrahydroimidazo[1,5-a]pyrimidin-6-amine;

the tautomers thereof; the stereoisomers thereof; or the pharmaceutically acceptable salts thereof.

Advantageously, the present invention provides a process for the preparation of a compound of formula I which comprises reacting a compound of formula II wherein Hal is Cl or Br with a compound of formula III wherein W is $B(OH)_2$, $Sn(Bu)_3$ or $Sn(CH_3)_3$ in the presence of a palladium catalyst and an inorganic base optionally in the presence of a solvent. The process is shown in flow diargram I, wherein Hal and W are as defined hereinabove.

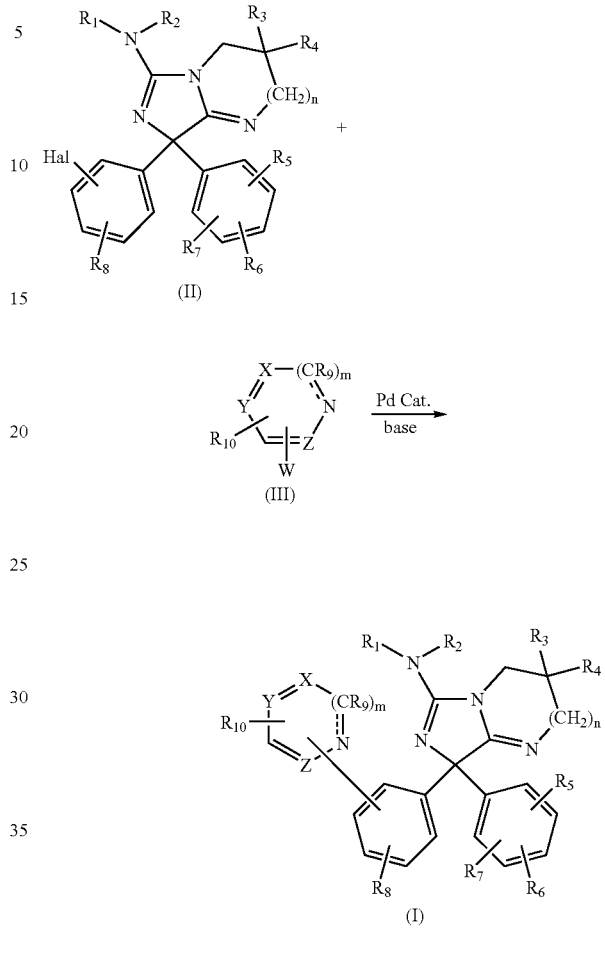

Palladium catalysts suitable for use in the process of the invention include Pd(0) or Pd(II) catalysts such as dichlorobis(tri-o-tolylphosphine)palladium(II), $Pd(OCOCH_3)_2$/tri-o-tolylphosphine, tetrakis(triphenylphosphine)palladium(0), tris(dibenzylideneacetone)dipalladium(0)triphenylphosphine, or the like.

Inorganic bases suitable for use in the inventive process include Na or K hydroxides, carbonates or bicarbonates, preferably $Na_2CO_3$ or $K_2CO_3$.

Solvents suitable for use in the inventive process include polar or non-polar organic solvents such as toluene, diethoxy ethyl ether, dioxane, ethyleneglycol dimethyl ether or any non-reactive organic solvent which is capable of solubilizing the formula II or formula III compounds.

Compounds of formula II may be prepared using conventional synthetic methods and, if required, standard separation or isolation techniques. For example, compounds of formula II wherein $R_1$ and $R_2$ are H (IIa), may be prepared by reacting a ketone of formula IV with a phenyl magnesium bromide of formula V in the presence of a catalyst such as CuI to give a 1,1,1-trisubstituted methanol compound of formula VI; reacting said formula VI methanol sequentially with thionyl chloride and ammonia to give the corresponding methylamine of formula VII; and reacting said formula VII amine with cyanogen bromide in the presence of acetonitrile to give the desired formula IIa product. The reaction is shown in flow diagram II wherein Hal is Cl or Br.

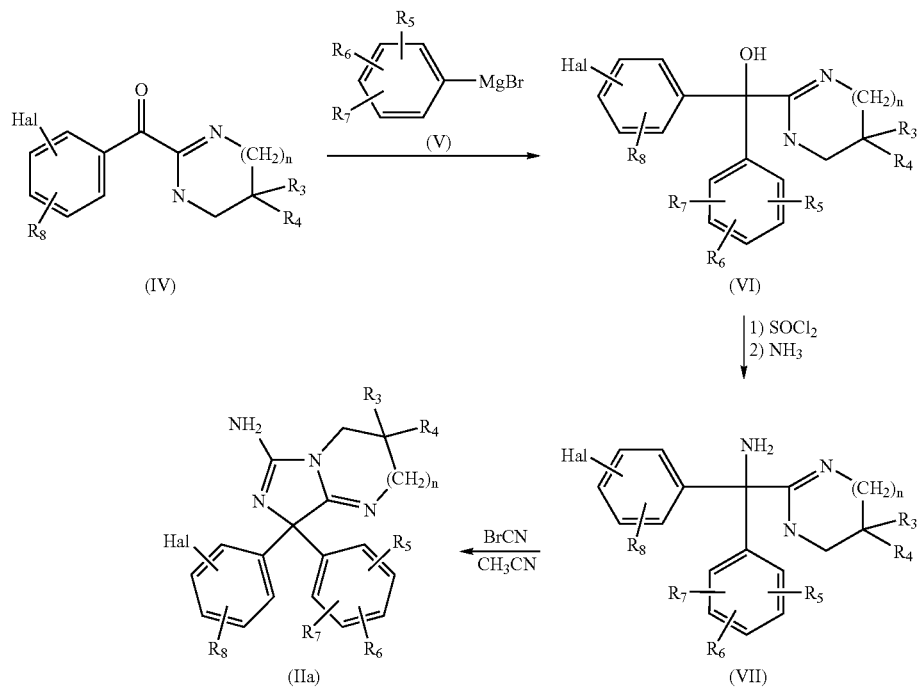

Ketones of formula IV may be prepared using conventional techniques, for example, by reacting a benzoyl halide of formula VIII with an imidazole or tetrahydropyrimidine of formula IX in the presence of a base such as NaOH, or by oxidizing the appropriate methanol compound of formula X with an oxidizing agent such as MnO2. The reactions are shown in flow diagram III.

Flow Diagram III

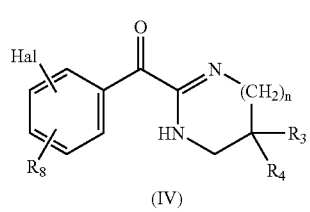

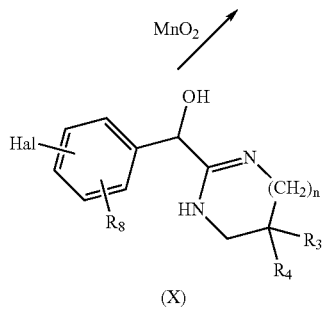

Compounds of formula X may be prepared by reacting a benzaldehyde of formula XI with $NaHSO_3$ and NaCN to give the corresponding cyanomethanol of formula XII; reacting said formula XII compound with ethanol and HCl to give the imidate of formula XIII; and reacting said formula XIII compound with a diamine of formula XIV to give the desired methanol derivative of formula X. The reaction is shown in flow diagram IV wherein Hal is Cl or Br.

Flow Diagram IV

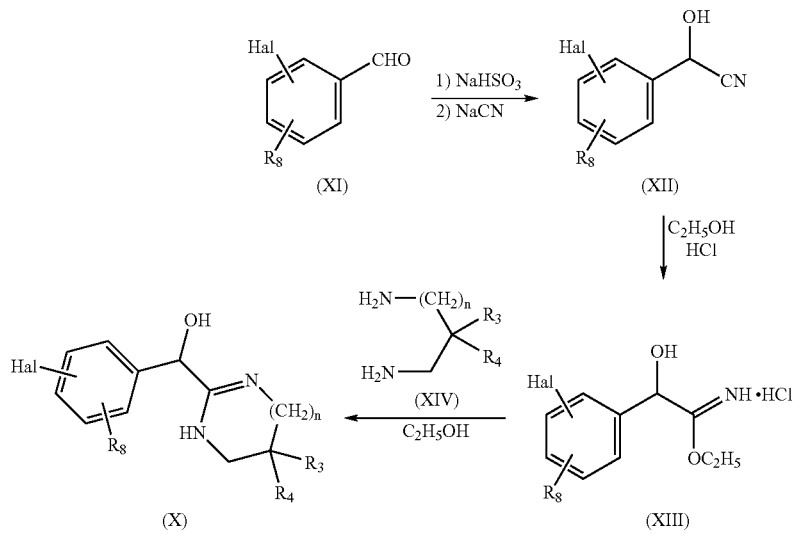

Compounds of formula IIa may be converted to the corresponding compounds of formula I wherein $R_1$ and $R_2$ are H using the procedure described hereinabove in flow diagram I.

Compounds of formula I wherein $R_1$ and $R_2$ are other than H may be prepared using standard alkylation techniques such as reacting the compound of formula I wherein $R_1$ and $R_2$ are H with an alkyl halide, $R_1$-Hal, to give the compound of formula I wherein $R_2$ is H (Id) and optionally reacting said formula Id compound with a second alkyl halide, $R_2$-Hal, to give the desired formula I compound wherein $R_1$ and $R_2$ are other than H.

Advantageously, the compounds of the invention are useful for the treatment, prevention or amelioration of a disease or disorder characterized by elevated β-amyloid deposits or β-amyloid levels in a patient, including Alzheimer's disease, Downs Syndrome, Hereditary Cerebral Hemorrhage with Amyloidosis of the Dutch type or other neurodegenerative or dementia-inducing disorders. Accordingly, the present invention provides a method for the treatment, prevention or amelioration of a disease or disorder characterized by elevated β-amyloid deposits or β-amyloid levels in a patient which comprises providing said patient with a therapeutically effective amount of a compound of formula I as described hereinabove. The compound may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

Alternatively, the use of sustained delivery devices may be desirable, in order to avoid the necessity for the patient to take medications on a daily basis. "Sustained delivery" is defined as delaying the release of an active agent, i.e., a compound of the invention, until after placement in a delivery environment, followed by a sustained release of the agent at a later time. Those of skill in the art know suitable sustained delivery devices. Examples of suitable sustained delivery devices include, e.g., hydrogels (see, e.g., U.S. Pat. Nos. 5,266,325; 4,959,217; and 5,292,515), an osmotic pump, such as described by Alza (U.S. Pat. Nos. 4,295,987 and 5,273,752) or Merck (European Patent No. 314,206), among others; hydrophobic membrane materials, such as ethylenemethacrylate (EMA) and ethylenevinylacetate (EVA); bioresorbable polymer systems (see, e.g., International Patent Publication No. WO 98/44964, Bioxid and Cellomeda; U.S. Pat. Nos. 5,756,127 and 5,854,388); other bioresorbable implant devices have been described as being composed of, for example, polyesters, polyanhydrides, or lactic acid/glycolic acid copolymers (see, e.g., U.S. Pat. No. 5,817,343 (Alkermes Inc.)). For use in such sustained delivery devices, the compounds of the invention may be formulated as described herein.

In another aspect, the invention provides a pharmaceutical kit for delivery of a product. Suitably, the kit contains packaging or a container with the compound formulated for the desired delivery route. For example, if the kit is designed for administration by inhalation, it may contain a suspension containing a compound of the invention formulated for aerosol or spray delivery of a predetermined dose by inhalation. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the spray pump or other delivery device.

Other suitable components to such kits will be readily apparent to one of skill in the art, taking into consideration the desired indication and the delivery route. The doses may be repeated daily, weekly, or monthly, for a predetermined length of time or as prescribed.

For a more clear understanding, and in order to illustrate the invention more clearly, specific examples thereof are set forth hereinbelow. The following examples are merely illustrative and are not to be understood as limiting the scope and underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

Unless otherwise noted, all parts are parts by weight. The term NMR designates nuclear magnetic resonance. The terms THF and DMF designate tetrahydrofuran and dimethyl formamide, respectively.

EXAMPLE 1

Preparation of 2-(3-Bromobenzoyl)-1H-imidazole

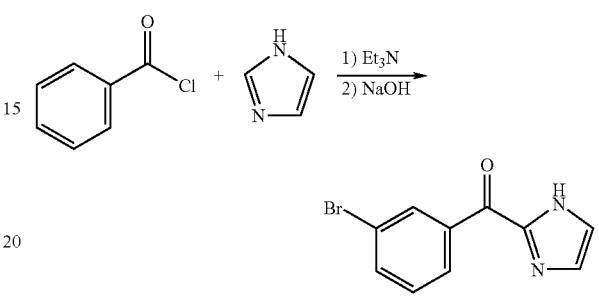

A solution of imidazole (2.66 g, 39.1 mmol) and triethylamine ($Et_3N$) 8.03 g, 79.4 mmol) in pyridine at 0° C. is treated with 3-bromobenzoyl chloride (17.5 g, 79.9 mmol), stirred for 5 min, allowed to warm to room temperature for 45 min, treated with an aqueous sodium hydroxide solution (7.5 N, 20 mL, 150 mmol), heated at reflux temperature for 2 h, cooled to room temperature, diluted with water, further cooled with an ice bath for 1 h and filtered. The filtercake is washed with water and dried under vacuum at 50° C. overnight to afford the title compound as a light tan solid, 4.89 g (50% yield), identified by NMR and mass spectral analyses. $^1$H NMR (500 MHz, $CDCl_3$) δ 10.58 (br s, 1H), 8.73 (t, J=1.8 Hz, 1H), 8.61 (dt, J=7.8, 1.2 Hz, 1H), 7.75-7.72 (m, 1H), 7.42-7.38 (m, 2H), 7.32 (s, 1H); ESI MS m/z 250 $[C_{10}H_7BrN_2O+H]^+$.

EXAMPLE 2

Preparation of 1-(3-Bromophenyl)-1-(imidazol-2-yl)-1-[4-(trifluoromethoxy)phenyl]methanol

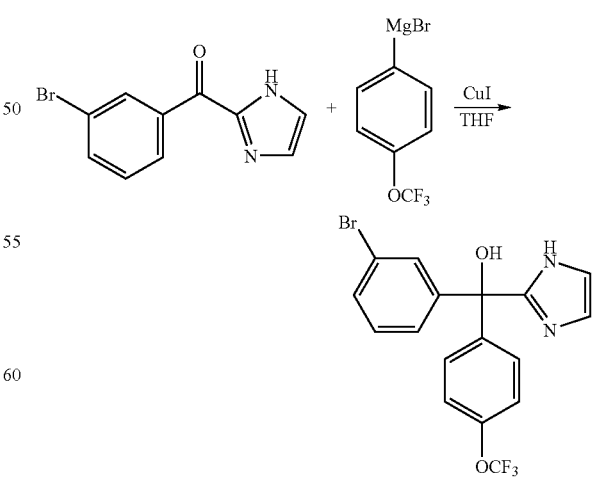

A mixture of magnesium (0.644 g, 87.7 mmol) in THF (13 mL) at 50° C. is treated dropwise with a solution of 1-bromo- 4-(trifluoromethoxy)benzene (6.32 g, 26.2 mmol) in THF over a period of 5 min, stirred at 50° C. for an additional 1.5 h, cooled to room temperature, treated with copper(I) iodide (0.041 g, 0.215 mmol) and a solution of 2-(3-bromobenzoyl)-1H-imidazole (2.60 g, 10.4 mmol) in THF, heated at 65° C. overnight, cooled to room temperature and diluted with a 1:1:1 mixture of ethyl acetate, water and saturated aqueous ammonium chloride. The phases are separated and the aqueous phase is extracted with ethyl acetate. The combined organic extracts are dried over sodium sulfate, filtered and concentrated. The resultant residue is purified by flash chromatography (silica, 85:15 to 75:25 hexanes/ethyl acetate as eluent) affords the title product as a yellow solid, 3.47 g (81% yield), identified by NMR and mass spectral analyses. $^1$H NMR (500 MHz, CDCl$_3$) δ 8.98 (br s, 1H), 7.55 (t, J=1.6 Hz, 1H), 7.45 (dt, J=8.1, 1.9 Hz, 1H), 7.37-7.34 (m, 2H), 7.24-7.20 (m, 2H), 7.18 (d, J=8.1 Hz, 2H), 7.07 (br s, 1H), 6.98 (br s, 1H), 4.30 (br s, 1H); ESI MS m/z 412 [C$_{17}$H$_{12}$BrF$_3$N$_2$O$_2$+H]$^+$.

EXAMPLE 3

Preparation of 1-(3-Bromophenyl)-1-(imidazol-2-yl)-1-[4-(trifluoromethoxy)phenyl]methylamine

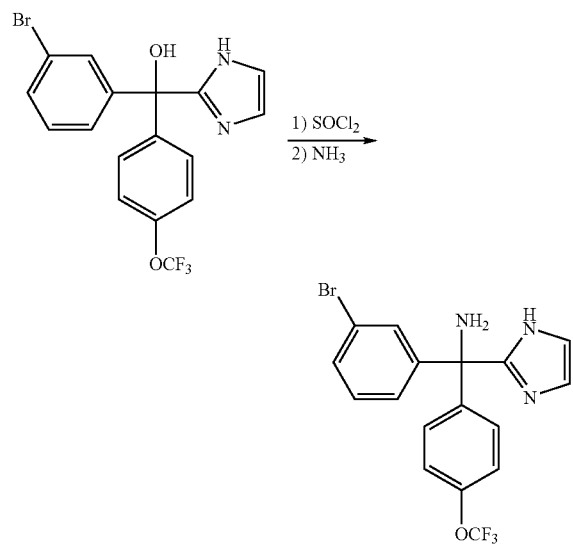

A mixture of 1-(3-bromophenyl)-1-(imidazol-2-yl)-1-[4-(trifluoromethoxy)phenyl]methanol (1.89 g, 4.57 mmol) and thionyl chloride (2.13 g, 17.9 mmol) in benzene is heated at 80° C. for 3 h, cooled to room temperature and concentrated in vacuo to dryness. This orange solid residue is dispersed in isopropanol, bubbled with ammonia gas at ice-bath temperature until the solution is saturated. This ammonia saturated solution is heated in a sealed tube at 35° C. overnight, cooled to room temperature, concentrated and partitioned between chloroform (50 mL) and 1 N HCl (50 mL). The phases are separated and the organic phase is washed with additional 1 N HCl. The combined HCl washes are cooled to 0° C., basified to pH>10 by the addition of solid sodium hydroxide and extracted with chloroform. The combined chloroform extracts are dried over sodium sulfate, filtered and concentrated to afford the title product as a light yellow solid, 1.68 g (89% yield), identified by NMR and mass spectral analyses. $^1$H NMR (500 MHz, CDCl$_3$) δ 9.12 (br s, 1H), 7.51 (t, J=1.2 Hz, 1H), 7.44-7.41 (m, 1H), 7.35-7.31 (m, 2H), 7.22-7.19 (m, 2H), 7.18-7.15 (m, 2H), 7.15 (t, J=1.5 Hz, 1H), 6.97 (t, J=1.7 Hz, 1H), 2.48 (br s, 2H); ESI MS m/z 412 [C$_{17}$H$_{13}$BrF$_3$N$_3$O+H]$^+$.

EXAMPLE 4

Preparation of 7-(3-(Bromophenyl)-7-[4-(trifluoromethoxy)phenyl]-7H-imidazo[1,5-a]imidazol-5-ylamine

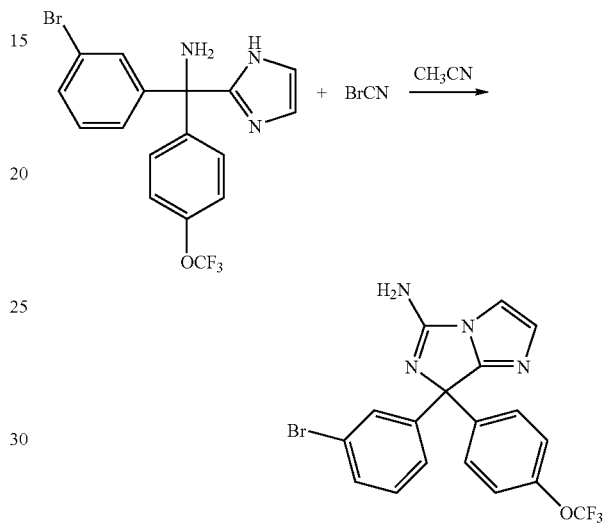

A mixture of 1-(3-bromophenyl)-1-(imidazol-2-yl)-1-[4-(trifluoromethoxy)phenyl]methylamine (1.67 g, 4.05 mmol) and cyanogen bromide (1.75 g, 16.5 mmol) in acetonitrile is heated at 100° C. in a sealed tube overnight, cooled to room temperature and concentrated. The resultant residue is purified twice by flash chromatography (silica, 96:4:0.5 methylene chloride/methanol/concentrated ammonium hydroxide, then 85:15 to 50:50 hexanes/ethyl acetate as eluent) to afford the title compound as a yellow solid 0.671 g (38% yield), identified by NMR and mass spectral analyses. $^1$H NMR (500 MHz, CDCl$_3$) δ 7.61 (t, J=1.6 Hz, 1H), 7.53-7.48 (m, 2H), 7.46-7.41 (m, 3H), 7.27-7.22 (m, 4H); ESI MS m/z 437 [C$_{18}$H$_{12}$BrF$_3$N$_4$O+H]$^+$.

EXAMPLE 5

Preparation of 7-[(3-(Pyrimidin-5-yl)phenyl]-7-[4-(trifluoromethoxy)phenyl]-7H-imidazo[1,5-a]imidazol-5-ylamine

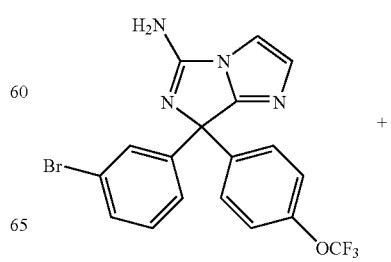

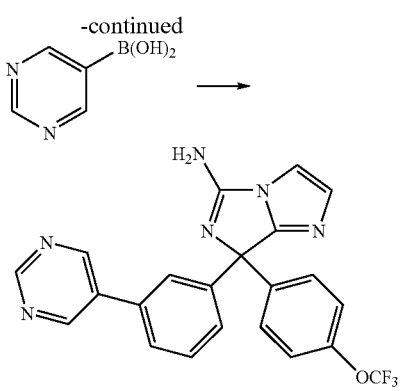

A mixture of 7-(3-(bromophenyl)-7-[4-(trifluoromethoxy)phenyl]-7H-imidazo[1,5-a]imidazol-5-ylamine (0.201 g, 0.460 mmol), 5-pyrimidine boronic acid (0.073 g, 0.587 mmol), bis(triphenylphosphino)palladium(II) chloride (0.016 g, 0.0232 mmol), triphenylphosphine (0.012 g, 0.047 mmol) and potassium carbonate (0.189 g, 1.37 mmol) in 5:1 dioxane/water is heated at 100° C. for 3.5 h, cooled to room temperature and concentrated. The resultant residue is purified by flash chromatography (silica, 96:4:0.5 methylene chloride/methanol/concentrated ammonium hydroxide as eluent) to afford the title compound as an off-white solid, 0.037 g (19% yield), mp 120-130° C.; identified by NMR and mass spectral analyses.

$^1$H NMR (500 MHz, CD$_3$OD) δ 9.12 (s, 1H), 9.02 (s, 2H), 7.81 (s, 1H), 7.67-7.62 (m, 2H), 7.56-7.51 (m, 3H), 7.47 (d, J=1.1 Hz, 1H), 7.27 (d, J=1.5 Hz, 1H), 7.23 (d, J=8.3 Hz, 2H); IR (ATR) 3143, 1672, 1505, 1443, 1414, 1253, 1216, 1159, 791, 723 cm$^{-1}$; ESI MS m/z 437 [C$_{22}$H$_{15}$F$_3$N$_6$O+H]$^+$

EXAMPLE 6

Preparation of 1-(3-Bromo-4-fluorophenyl)-1-cyanomethanol

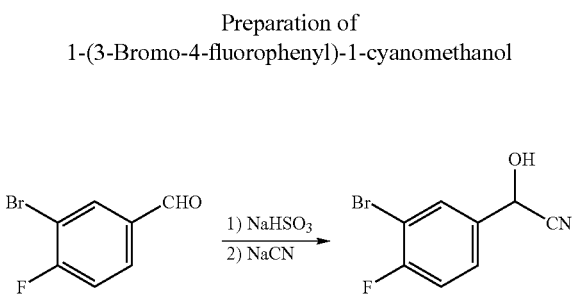

A solution of sodium bisulfite (28.3 g, 271 mmol) in water at 50° C. is treated with 3-bromo-4-fluorobenzaldehyde (45.8 g, 225 mmol), stirred at 50° C. for 2 h, cooled with an ice bath, diluted with ether, treated dropwise with an aqueous solution of sodium cyanide (12.2 g, 248 mmol) over a period of 30 min and stirred at room temperature overnight. The reaction mixture is separated, and the aqueous phase is extracted with ether. The extracts are combined with the organic phase, washed with brine, dried over magnesium sulfate and concentrated to dryness to afford the title compound as a clear oil, 47.6 g (92% yield), identified by NMR analysis. $^1$H NMR (300 MHz, CDCl$_3$) δ 7.75 (m, 1H), 7.47 (m, 1H), 7.23 (m, 1H), 5.54 (m, 1H), 3.19 (m, 1H).

EXAMPLE 7

Preparation of Ethyl 2-(3-Bromo-4-fluorophenyl)-2-hydroxyethanimidoate Hydrochloride

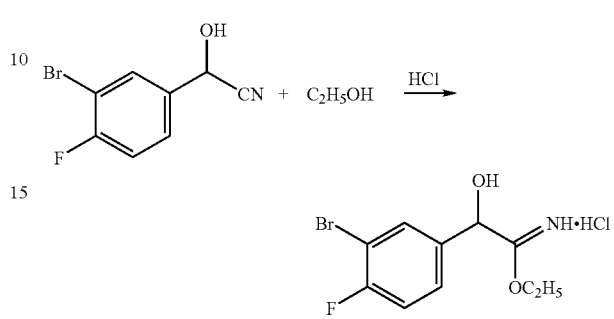

A solution of 1-(3-bromo-4-fluorophenyl)-1-cyanomethanol (47.5 g, 206 mmol) and ethanol (10.9 g, 237 mmol) in ether is cooled with an ice bath and treated dropwise with HCl (258 mL of a 1.0 M solution in diethyl ether, 258 mmol) over a period of 40 min., stirred at ice-bath temperature for 2 h, stored at 0° C. for 6 days, warmed to room temperature, diluted with hexanes and filtered. The filtercake is dried to afford the title compound as a white solid, 39.8 g (62% yield), identified by NMR and mass spectral analyses. The title compound is a mixture of E and Z isomers. $^1$H NMR (300 MHz, CD$_3$OD) δ 7.78 (m, 1H), 7.49 (m, 1H), 7.28 (m, 1H), 5.54 and 5.17 (2m, 1H), 4.45 and 4.15 (2m, 2H), 1.38 and 1.20 (2t, 3H); ESI MS m/z 261 [C$_{10}$H$_{11}$BrFNO$_2$+H]$^+$

EXAMPLE 8

Preparation of 1-(3-Bromo-4-fluorophenyl)-1-(2-tetrahydropyrimidinyl)methanol

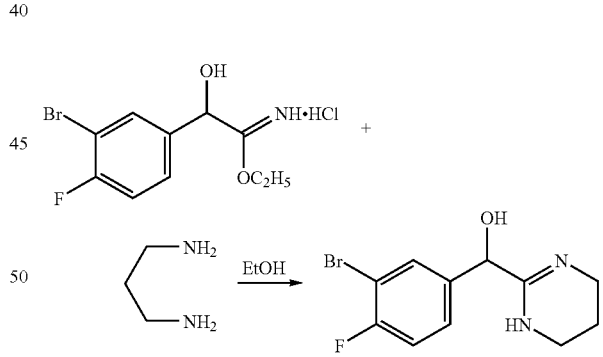

A mixture of ethyl 2-(3-bromo-4-fluorophenyl)-2-hydroxyethanimidoate Hydrochloride (39.8 g, 127 mmol) and 1,3-diaminopropane (9.43 g, 127 mmol) in ethanol is heated at 120° C. in a sealed tube overnight, cooled to room temperature, concentrated to remove the solvent, diluted with water, stirred vigorously for 1 h and filtered. The filtrate is cooled with an ice bath, made strongly basic with 1 N NaOH, cooled for 1 h in an ice bath and filtered. The filtercake is dried to afford th title compound as a white solid 23.4 g (64% yield), identified by NMR and mass spectral analyses. $^1$H NMR (500 MHz, CDCl$_3$) δ 7.59 (m, 1H), 7.30 (m, 1H), 7.10 (t, J=8.4 Hz, 1H), 4.79 (s, 1H), 3.35 (m, 4H), 1.76 (m, 2H); ESI MS m/z 287 [C$_{11}$H$_{12}$BrFN$_2$O+H]$^+$.

EXAMPLE 9

Preparation of 2-(3-Bromo-4-fluorobenzoyl)-2,3,4,5-tetrahydropyrimidine

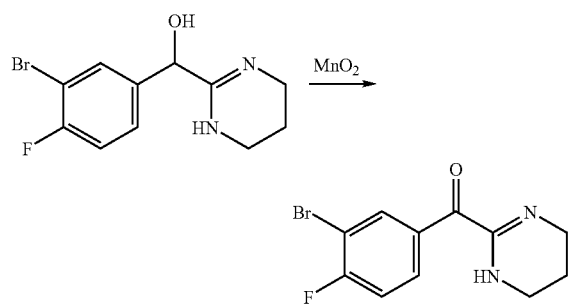

A mixture of 1-(3-bromo-4-fluorophenyl)-1-(2-tetrahydropyrimidinyl)methanol (23.4 g, 81.5 mmol) and manganese dioxide (70.8 g, 815 mmol) in methylene chloride is stirred at room temperature for 3 days and filtered through diatomaceous earth. The filtercake is washed with chloroform. The filtrates are combined and concentrated to dryness to afford the title compound as a yellow-green solid, 18.9 g (81% yield), identified by NMR and mass spectral analyses. $^1$H NMR (500 MHz, CDCl$_3$) δ 8.51 (m, 1H), 8.23 (m, 1H), 7.15 (t, J=8.4 Hz, 1H), 6.10 (br s, 1H), 3.65 (br s, 2H), 3.41 (br s, 2H), 1.83 (m, 2H); ESI MS m/z 284 [C$_{11}$H$_{10}$BrFN$_2$O+H]$^+$.

EXAMPLE 10

Preparation of 1-(3-Bromo-4-fluorophenyl)-1-(tetrahydropyrimidin-2-yl)-1-[4-(trifluoromethoxy)phenyl]methanol

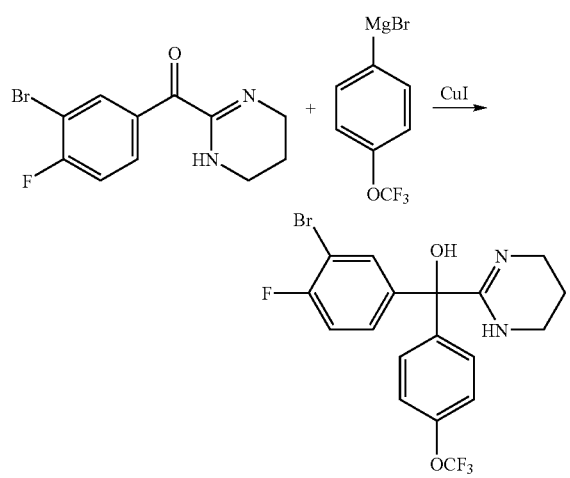

A mixture of magnesium (2.13 g, 87.7 mmol) in THF at 50° C. is treated dropwise with a solution of 1-bromo-4-(trifluoromethoxy)benzene (21.1 g, 87.7 mmol) in THF over a period of 20 min., stirred at 50° C. for an additional 1.5 h, cooled to room temperature, treated with copper(I) iodide (0.13 g, 0.70 mmol) and a solution of 2-(3-bromo-4-fluorobenzoyl)-2,3,4,5-tetrahydropyrimidine (10.0 g, 14.9 mmol) in THF, heated at 65° C. overnight, cooled to room temperature and diluted with ethyl acetate and saturated aqueous ammonium chloride. The phases are separated. The organic phase is washed sequentially with water and brine, dried over sodium sulfate, and concentrated to afford 18.5 g of a brown oil. The oil is purified by flash chromatography (silica, 90:10:0.5 methylene chloride/methanol/concentrated ammonium hydroxide as eluent) to afford the title compound as a yellow oil, 10.0 g (64% yield), identified by NMR and mass spectral analyses. $^1$H NMR (300 MHz, CDCl$_3$) δ 7.60 (dd, J=6.4, 2.3 Hz, 1H), 7.41 (dd, J=6.9, 2.0 Hz, 2H), 7.28-7.20 (m, 3H), 7.10 (t, J=8.3 Hz, 1H), 3.50 (m, 6H), 1.96 (m, 2H); ESI MS m/z 447 [C$_{18}$H$_{15}$BrF$_4$N$_2$O$_2$+H]$^+$.

EXAMPLE 11

Preparation of 1-(3-Bromo-4-fluorophenyl)-1-(tetrahydropyrimidin-2-yl)-1-[4-(trifluoromethoxy)phenyl]methylamine

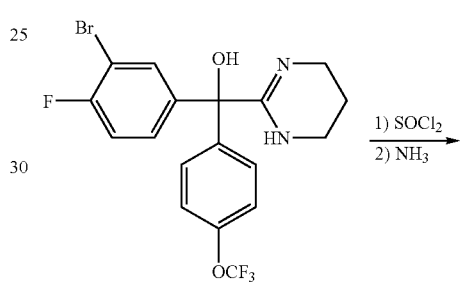

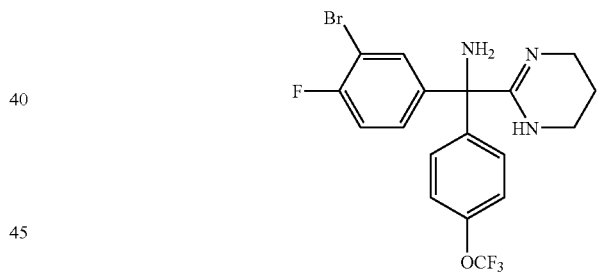

A mixture of 1-(3-bromo-4-fluorophenyl)-1-(tetrahydropyrimidin-2-yl)-1-[4-(trifluoromethoxy)phenyl]methanol (4.60 g, 10.3 mmol) and thionyl chloride (12.2 g, 103 mmol) in toluene is heated at 110° C. overnight, cooled to room temperature and concentrated to dryness to give a tan solid residue. The residue is dispersed in isopropanol and bubbled through with ammonia gas until the mixture is saturated with ammonia. The saturated mixture is heated in a sealed tube at 45° C. overnight, cooled to room temperature and concentrated. The resultant residue is partitioned between chloroform and 1 N NaOH. The aqueous phase is separated and extracted with chloroform. The extracts are combined with the organic phase, dried over potassium carbonate and concentrated to afford the title compound as a dark oil, 0.89 g (>100%, ~80% purity), identified by NMR and mass spectral analyses. $^1$H NMR (300 MHz, CDCl$_3$) δ 7.65 (m, 1H), 7.41-7.303 (m, 36H), 3.41 (br s, 4H), 2.32 (br s, 2H), 1.77 (m, 2H); ESI MS m/z 446 [C$_{18}$H$_{16}$BrF$_4$N$_3$O+H]$^+$.

EXAMPLE 12

Preparation of 8-(3-Bromo-4-fluorophenyl)-8-[4-(trifluoromethoxy)phenyl]-2,3,4,8-tetrahydroimidazo[1,5-a]pyrimidin-6-ylamine

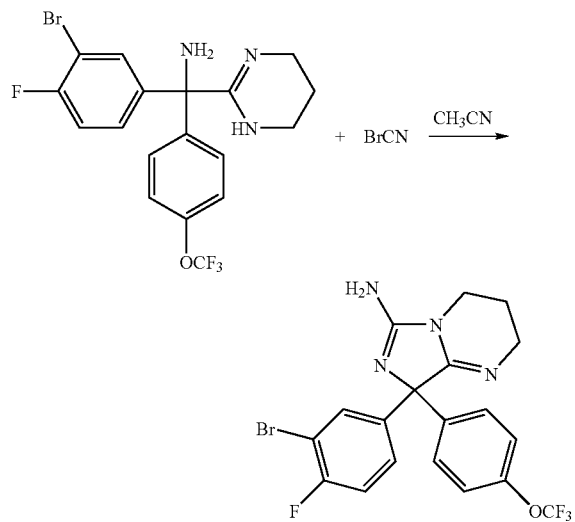

A mixture of 1-(3-bromo-4-fluorophenyl)-1-(tetrahydropyrimidin-2-yl)-1-[4-(trifluoromethoxy)phenyl]methylamine (0.85 g, ~80% purity, ~1.52 mmol) and cyanogen bromide (0.81 g, 7.62 mmol) in acetonitrile is stirred at room temperature for 45 min, heated at 100° C. in a sealed tube overnight, cooled to room temperature and concentrated. The resultant residue is purified by flash chromatography (silica, 95:5:0.25 methylene chloride/methanol/concentrated ammonium hydroxide as eluent) to afford the title compound as a tan solid, 0.26 g (36% yield), identified by NMR and mass spectral analyses. $^1$H NMR (300 MHz, CDCl$_3$) δ 7.74 (dd, J=6.7, 2.3 Hz, 1H), 7.49 (dd, J=6.7, 2.1 Hz, 2H), 7.38 (m, 1H), 7.13 (d, J=8.1 Hz, 2H), 7.03 (t, J=8.5 Hz, 1H), 3.58 (m, 4H), 1.86 (m, 2H); ESI MS m/z 471 [C$_{19}$H$_{15}$BrF$_4$N$_4$O+H]$^+$.

EXAMPLE 13

Preparation of 8-{[(4-Fluoro-3-pyrimidin-5-yl)phenyl]-8-[4-(trifluoromethoxy)phenyl]-2,3,4,8-tetrahydroimidazo[1,5-a]pyrimidin-6-yl}amine

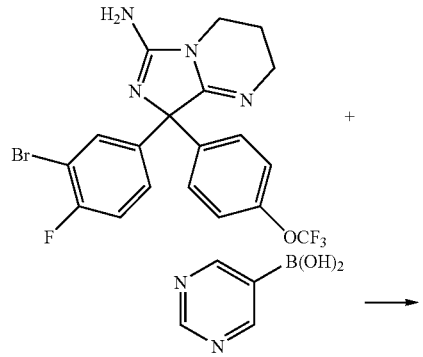

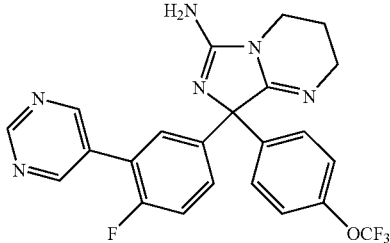

A mixture of 8-(3-bromo-4-fluorophenyl)-8-[4-(trifluoromethoxy)phenyl]-2,3,4,8-tetrahydroimidazo[1,5-a]pyrimidin-6-ylamine (0.26 g, 0.552 mmol), 5-pyrimidine boronic acid (0.082 g, 0.662 mmol), tetra(kistriphenylphosphino)palladium(0) (0.032 g, 0.0276 mmol) and potassium carbonate (0.23 g, 1.65 mmol) in 5:1 dioxane/water is heated at 100° C. for 1 h, treated with additional tetra(kistriphenylphosphino)palladium(0) (0.032 g, 0.0276 mmol), heated at 100° C. for 3.5 h, cooled to room temperature and concentrated. The resultant residue is purified by flash chromatography (silica, 95:5:0.25 methylene chloride/methanol/concentrated ammonium hydroxide as eluent) to afford the title compound as an off-white solid, 0.079 g (30% yield), mp 105-115° C., identified by NMR and mass spectral analyses. $^1$H NMR (300 MHz, CD$_3$OD) ▭9.14 (s, 1H), 8.97 (s, 2H), 7.55 (m, 2H), 7.43 (dd, J=6.8, 2.1 Hz, 2H), 7.21-7.31 (m, 3H), 3.69 (m, 2H), 3.50 (m, 2H), 1.87 (m, 2H); ESI MS m/z 471 [C$_{23}$H$_{18}$F$_4$N$_6$O+H]$^+$;

EXAMPLE 14

Preparation of {8-[4-Fluoro-3-(5-fluoropyrimidin-3-yl)phenyl]-8-[4-(trifluoromethoxy)phenyl]-2,3,4,8-tetrahydroimidazo[1,5-a]pyrimidin-6-yl}amine

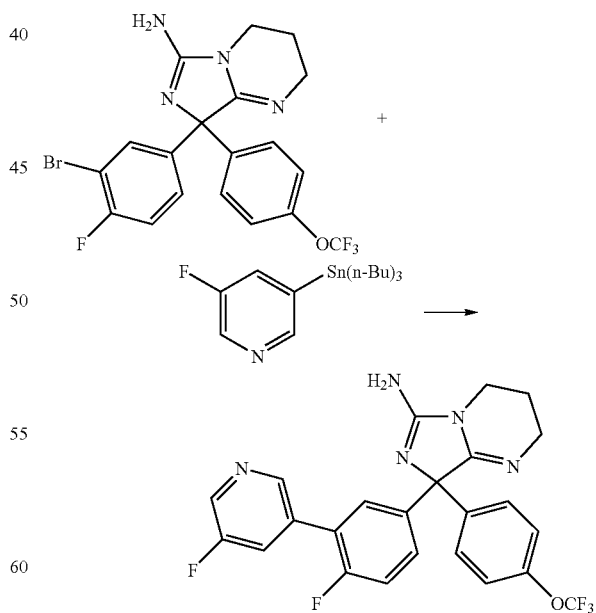

A mixture of 8-(3-bromo-4-fluorophenyl)-8-[4-(trifluoromethoxy)phenyl]-2,3,4,8-tetrahydroimidazo[1,5-a]pyrimidin-6-ylamine (0.075 g, 0.159 mmol), 3-fluoro-5-(tributylstannyl)pyridine (0.092 g, 0.239 mmol), and dichlorobis (triphenylphosphine)palladium(II) (0.006 g, 0.008 mmol) in DMF is degassed, heated at 150° C. in a sealed tube for 1.5 h, cooled to room temperature and diluted with ethyl acetate (50 mL) and 5% aqueous LiCl. The reaction mixture is separated. The organic phase is washed with 5% aqueous LiCl, dried over sodium sulfate and concentrated. The resultant residue is purified by flash chromatography (silica, 95:5:0.25 methylene chloride/methanol/concentrated ammonium hydroxide as eluent) to afford the title product as a white solid, 0.043 g (56% yield), mp 94-105° C.; identified by NMR and mass spectral analyses. $^1$H NMR (300 MHz, CD$_3$OD) 8.56 (d, J=1.3 Hz, 1H), 8.47 (d, J=2.6 Hz, 1H), 7.83 (d, J=9.7 Hz, 1H), 7.54-7.44 (m, 4H), 7.41-7.21 (m, 3H), 3.69 (m, 2H), 3.50 (m, 2H), 1.87 (m, 2H); ESI MS m/z 488 [C$_{24}$H$_{18}$F$_5$N$_5$O+H]$^+$;

EXAMPLES 15-28

Preparation of Diphenylimidazopyrimidinylamine Derivatives

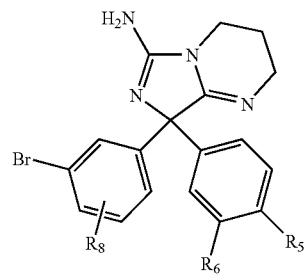

+

Using essentially the same procedures described in Examples 5, 13 and 14 hereinabove and employing the appropriate azacyclic reagent wherein W is B(OH)$_2$ or Sn(n-Bu)$_3$, the compounds on Table I were obtained and identified by NMR and mass spectral analyses.

TABLE I

| Ex. No. | R5 | R6 | R8 | R10 | X | mp ° C. |
|---|---|---|---|---|---|---|
| 15 | OCF$_3$ | H | 4-F | 2-F | C—H | 99-122 |
| 16 | OCF$_3$ | H | H | H | N | 214-218 |
| 17 | OCF$_3$ | H | H | 2-F | C—H | 105-115 |
| 18 | OCF$_3$ | H | 4-F | 6-F | C—H | 110-115 |
| 19 | OCF$_3$ | H | H | H | C—F | 112-118 |
| 20 | OCF$_3$ | H | H | H | C—Cl | 112-116 |
| 21 | OCH$_3$ | H | H | 2-F | C—H | 117-121 |
| 22 | OCH$_3$ | H | H | H | N | 136-140 |
| 23 | OCH$_3$ | H | 4-F | H | N | 122 |
| 24 | OCH$_3$ | H | 4-F | 2-F | C—H | 115 |
| 25 | OC$_2$H$_5$ | OC$_2$H$_5$ | H | 2-F | C—H | 202-208 |
| 26 | OCHF$_2$ | H | H | 4-F | C—H | 81-92 |
| 27 | OCF$_3$ | H | H | 4-F | C—H | 83-97 |
| 28 | OCF$_3$ | H | H | 2-F | C—F | 94-102 |

EXAMPLE 29

Preparation of 8-(3-Pyrimidin-5-yl-phenyl)-8-(4-trifluoromethoxy-phenyl)-2,3,4,8-tetrahydro-imidazo[1,5-a]pyrimidin-6-yl-cyanamide

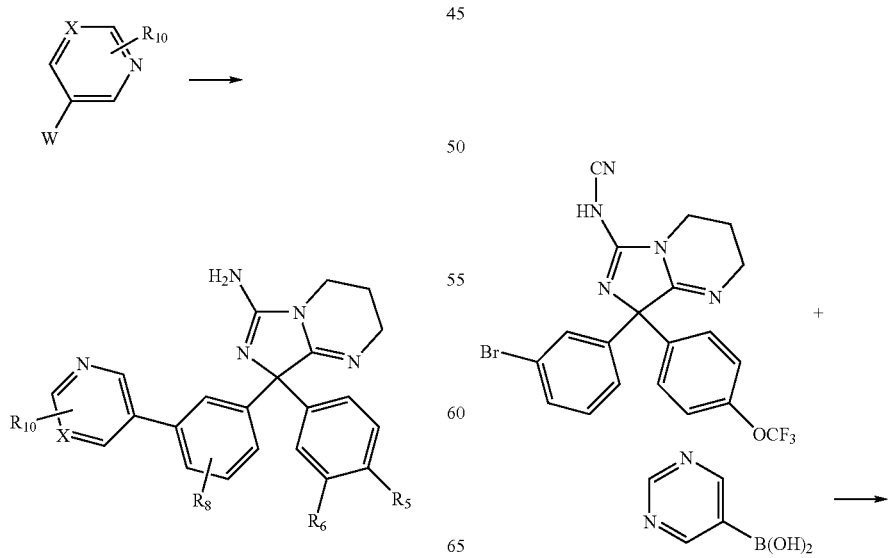

-continued

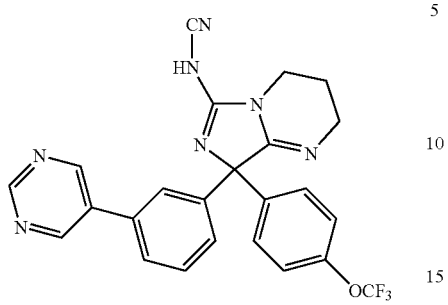

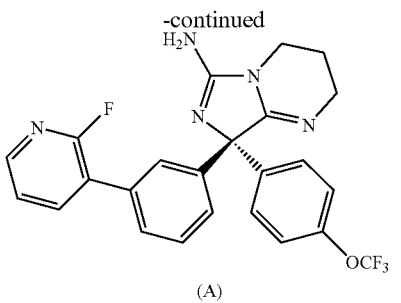

(A)

A mixture of ethylene glycol dimethyl ether, tris(dibenzylideneacetone)dipalladium (0) (0.014 g, 16.0 μmol), triphenylphosphine (0.008 g, 32.0 μmol) under a nitrogen atmosphere is stirred for 5 min., treated with 2 (0.153 g, 0.320 mmol), pyrimidine-5-boronic acid (0.047 g, 0.380 mmol), sodium carbonate (0.101 g, 0.96 mmol) and water (2 mL), heated at 85° C. for 1 hr, cooled to room temperature and concentrated. the resultant residue is purified by flash chromatography (silica, 97.5:2.5:0.5 methylene chloride/methanol/concentrated ammonium hydroxide as eluent) to afford the title compound as a white solid, 0.130 g (85% yield), mp 227-231° C.; identified by NMR and mass spectral analyses. $^1$H NMR (500 MHz, CD$_3$OD) δ 9.13 (s, 1H), 9.02 (s, 2H), 7.77 (d, J=7.5 Hz, 1H), 7.71 (s, 1H), 7.62 (dd, J=7.9, 7.6 Hz, 1H) 7.57 (d, J=8.0 Hz, 1H), 7.50 (d, J=8.9 Hz, 2H), 7.33 (d, J=8.3 Hz, 2H), 3.70 (m, 2H), 3.58 (m, 2H), 1.89 (m, 2H); IR (ATR) 3106, 2187, 1622, 1500, 1412, 1256, 1218, 1159 cm$^{-1}$; ESI MS m/z 478 [C$_{24}$H$_{18}$F$_3$N$_7$O+H

EXAMPLE 30

Preparation of (8R)-8-[3-(2-fluoropyridin-3-yl)phenyl]-8-[4-(trifluoromethoxy)phenyl]-2,3,4,8-tetrahydroimidazo[1,5-a]pyrimidin-6-amine (A) and (8S)-8-[3-(2-fluoropyridin-3-yl)phenyl]-8-[4-(trifluoromethoxy)phenyl]-2,3,4,8-tetrahydroimidazo[1,5-a]pyrimidin-6-amine (B)

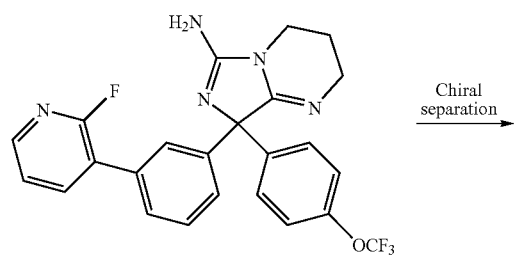 → Chiral separation (B)

A racemic mixture of 8-[3-(2-fluoropyridin-3-yl)phenyl]-8-[4-(trifluoromethoxy)phenyl]-2,3,4,8-tetrahydroimidazo[1,5-a]pyrimidin-6-amine-(0.740 g, 1.57 mmol) is placed on a Chiralpak AD 5×50 cm column (90:10:0.1 heptane/ethanol/diethylamine as eluent). The second eluting peak (t$_R$=26 min) is collected and concentrated to a pale yellow oil. The oil residue is re-dissolved in a minimal amount of methylene chloride, triturated with hexanes and filtered. The filtercake is dried under vacuum for 24 h to afford the title product A as an off-white solid, 0.299 g, mp 126-131° C.; [α]$^{25}$$_D$: −11.6° (c=0.5 in MeOH); identified by NMR, infrared and mass spectral analyses. $^1$H NMR (500 MHz, CD$_3$OD) δ 8.16 (dd, J=4.8, 1.1 Hz, 1H), 8.03-7.98 (m, 1H), 7.58 (s, 1H), 7.55-7.52 (m, 1H), 7.49-7.45 (m, 3H), 7.44-7.41 (m, 1H), 7.40-7.37 (m, 1H), 7.23 (d, J=8.2 Hz, 2H), 3.70 (t, J=6.0 Hz, 2H), 3.49 (t, J=5.4 Hz, 2H), 1.90-1.85 (m, 2H); IR (ATR) 3062, 2954, 1654, 1602, 1504, 1434, 1251, 1216, 1159, 791 cm$^{-1}$; ESI MS m/z 470 [C$_{24}$H$_{19}$F$_4$N$_5$O+H]$^+$;

The first eluting peak (t$_R$=19 min) is collected and concentrated to a pale yellow oil. The oil residue is re-dissolved in a minimal amount of methylene chloride, triturated with hexanes and filtered. The filtercake is dried under vacuum for 24 h to afford the title product B as an off-white solid, 0.315 g, mp 124-128° C.; [α]$^{25}$$_D$: +12.6° (c=0.5 in MeOH); identified by NMR, infrared and mass spectral analyses.

$^1$H NMR (500 MHz, CD$_3$OD) δ 8.16 (dd, J=4.8, 1.1 Hz, 1H), 8.03-7.98 (m, 1H), 7.58 (s, 1H), 7.55-7.52 (m, 1H), 7.49-7.45 (m, 3H), 7.44-7.41 (m, 1H), 7.40-7.37 (m, 1H), 7.23 (d, J=8.2 Hz, 2H), 3.70 (t, J=6.0 Hz, 2H), 3.49 (t, J=5.4 Hz, 2H), 1.90-1.85 (m, 2H); IR (ATR) 3064, 2947, 1653, 1602, 1504, 1434, 1251, 1216, 1158, 791 cm$^{-1}$; ESI MS m/z 470 [C$_{24}$H$_{19}$F$_4$N$_5$O+H]

EXAMPLE 31

Preparation of (8R)-8-(3-pyrimidin-5-ylphenyl)-8-[4-(trifluoromethoxy)phenyl]-2,3,4,8-tetrahydroimidazo[1,5-a]pyrimidin-6-amine (A) and (8S)-8-(3-pyrimidin-5-ylphenyl)-8-[4-(trifluoromethoxy)phenyl]-2,3,4,8-tetrahydroimidazo[1,5-a]pyrimidin-6-amine (B)

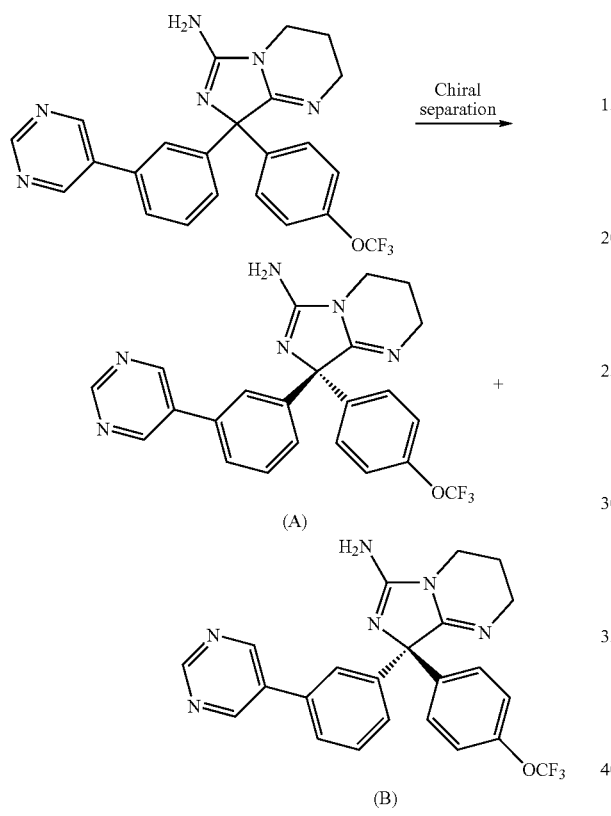

A racemic mixture of 8-(3-pyrimidin-5-ylphenyl)-8-[4-(trifluoromethoxy)phenyl]-2,3,4,8-tetrahydroimidazo[1,5-a]pyrimidin-6-amine-(2.0 g, 1.57 mmol) is placed on a Chiralpak AD 5×50 cm column (90:10:0.1 heptane/ethanol/diethylamine as eluent). The first eluting peak ($t_R$=34 min) is collected and concentrated to give a pale yellow oil. The oil is re-dissolved in a minimal amount of methylene chloride, triturated with hexanes and filtered. The filtercake is dried under vacuum for 24 h to afford the title compound A as an off-white solid, 0.815 g, mp 178-186° C.; $[\alpha]^{25}_D$: −14.7° (c=0.50 in MeOH); identified by NMR, infrared and mass spectral analyses. $^1$H NMR (500 MHz, CD$_3$OD) δ 9.12 (s, 1H), 9.02 (s, 2H), 7.70-7.67 (m, 2H), 7.57-7.51 (m, 2H), 7.48-7.44 (m, 2H), 7.26 (d, J=8.7 Hz, 2H), 3.73 (t, J=6.3 Hz, 2H), 3.55-3.52 (m, 2H), 1.92-1.88 (m, 2H); IR (ATR) 3040, 2956, 2859, 1655, 1504, 1413, 1253, 1160, 786 cm$^{-1}$; ESI MS m/z 453 [C$_{23}$H$_{19}$F$_3$N$_5$O+H]$^+$;

The second eluting peak ($t_R$=46 min) is collected and concentrated to give a pale yellow oil. The oil residue is re-dissolved in a minimal amount of methylene chloride, and then triturated with hexanes and filtered. The filtercake is dried under vacuum for 24 h to afford the title compound B as an off-white solid, 0.798 g, mp 180-186° C.; $[\alpha]^{25}_D$: +9.7° (c=0.51 in MeOH), identified by NMR, infrared and mass spectral analyses. $^1$H NMR (500 MHz, CD$_3$OD) δ9.13 (s, 1H), 9.02 (s, 2H), 7.73-7.69 (m, 2H), 7.58-7.51 (m, 2H), 7.49-7.46 (m, 2H), 7.29-7.26 (m, 2H), 3.76 (t, J=6.3 Hz, 2H), 3.57-3.55 (m, 2H), 1.93-1.90 (m, 2H); IR (ATR) 3040, 2955, 1655, 1553, 1505, 1413, 1253, 1201, 1162, 786 cm$^{-1}$; ESI MS m/z 453 [C$_{23}$H$_{19}$F$_3$N$_5$O+H]$^+$

EXAMPLE 32

Preparation of (8S)-8-[3-(5-Chloropyridin-3-yl)phenyl]-8-[4-(trifluoromethoxy)phenyl]-2,3,4,8-tetrahydroimidazo[1,5-a]pyrimidin-6-amine [A] and (8R)-8-[3-(5-Chloropyridin-3-yl)phenyl]-8-[4-(trifluoromethoxy)-phenyl]-2,3,4,8-tetrahydroimidazo[1,5-a]pyrimidin-6-amine [B]

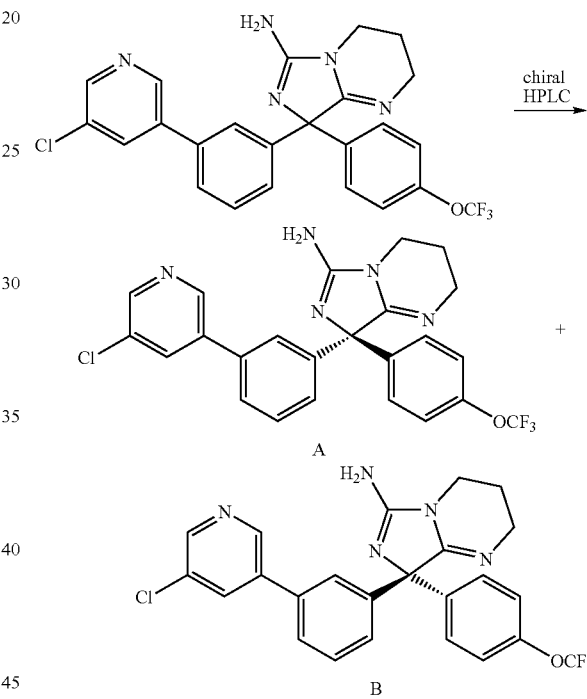

A racemic mixtue of 8-[3-(5-chloropyridin-3-yl)phenyl]-8-[4-(trifluoromethoxy)phenyl]-2,3,4,8-tetrahydroimidazo [1,5-a]pyrimidin-6-amine (1.73 g) was separated into its enantiomers using a Chiralpak AD 5×50 cm column (90:10:0.1 heptane/ethanol/diethylamine) to afford the title S-isomer (A) as an off-white solid, mp 104-116° C.; $[\alpha]^{25}_D$: −8.6° (c=0.51% in MeOH); $^1$H NMR (500 MHz, CD$_3$OD) δ8.69 (d, J=1.9 Hz, 1H), 8.53 (d, J=2.2 Hz, 1H), 8.11 (t, J=2.1 Hz, 1H), 7.69-7.67 (m, 1H), 7.65 (t, J=1.7 Hz, 1H), 7.54 (t, J=7.6 Hz, 1H), 7.51-7.45 (m, 3H), 7.29 (d, J=8.3 Hz, 2H), 3.77 (t, J=5.9 Hz, 2H), 3.58-3.55 (m, 2H), 1.97-1.92 (m, 2H); ESI MS m/z 486 [C$_{24}$H$_{19}$ClF$_3$N$_5$O+H]$^+$; and the title R-isomer (B) as an off-white solid, mp 114-118° C.; $[\alpha]^{25}_D$: +13.3° (c=0.53% in MeOH); $^1$H NMR (500 MHz, CD$_3$OD) □ 8.69 (d, J=1.9 Hz, 1H), 8.54 (d, J=2.3 Hz, 1H), 8.11 (t, J=2.1 Hz, 1H), 7.70-7.67 (m, 1H), 7.65 (t, J=1.6 Hz, 1H), 7.55 (t, J=7.7 Hz, 1H), 7.52-7.46 (m, 3H), 7.29 (d, J=8.2 Hz, 2H), 3.77 (t, J=6.0 Hz, 2H), 3.59-3.56 (m, 2H), 1.95-1.90 (m, 2H); ESI MS m/z 486 [C$_{24}$H$_{19}$ClF$_3$N$_5$O+H]$^+$.

EXAMPLE 33

Preparation of (8S)-8-[3-(4-fluoropyridin-3-yl)phenyl]-8-[4-(trifluoromethoxy)phenyl]-2,3,4,8-tetrahydroimidazo[1,5-a]pyrimidin-6-amine [A] and (8R)-8-[3-(4-fluoropyridin-3-yl)phenyl]-8-[4-(trifluoromethoxy)phenyl]-2,3,4,8-tetrahydroimidazo[1,5-a]pyrimidin-6-amine [B]

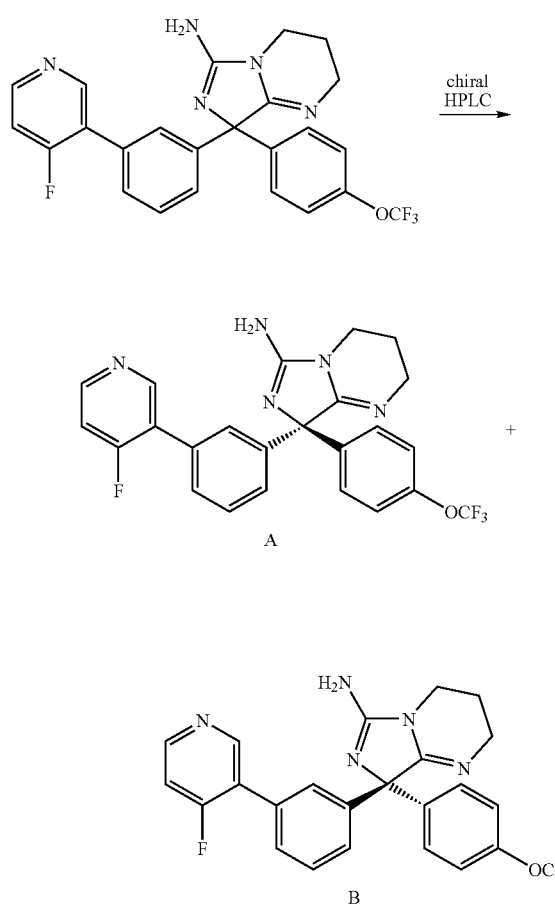

A racemic mixture of 8-[3-(4-fluoropyridin-3-yl)phenyl]-8-[4-(trifluoromethoxy)phenyl]-2,3,4,8-tetrahydroimidazo[1,5-a]pyrimidin-6-amine (1.89 g) was separated into its enantiomers using a Chiralpak AD 5×50 cm column (93:7:0.1 heptane/ethanol/diethylamine) to give the title S-isomer (A) as an off-white solid (0.755 g), mp 171° C.; $[\alpha]^{25}_D$: +10.6° (c=0.5% in MeOH); $^1$H NMR (500 MHz, CD$_3$OD) δ 8.63 (d, J=10.0 Hz, 1H), 8.52 (dd, J=7.3, 5.7 Hz, 1H), 7.57-7.52 (m, 2H), 7.51-7.45 (m, 4H), 7.32 (dd, J=10.3, 5.7 Hz, 1H), 7.24 (d, J=8.1 Hz, 2H), 3.71 (t, J=5.9 Hz, 2H), 3.50 (t, J=5.5 Hz, 2H), 1.90-1.85 (m, 2H); ESI MS m/z 470 [C$_{24}$H$_{19}$F$_4$N$_5$O+H]$^+$; and the title R-isomer (B) as an off-white solid (0.675 g), mp 115-116° C.; $[\alpha]^{25}_D$: −10.9° (c=0.5% in MeOH); $^1$H NMR (500 MHz, CD$_3$OD) □ 8.63 (d, J=10.1 Hz, 1H), 8.53 (dd, J=7.3, 5.7 Hz, 1H), 7.57-7.54 (m, 2H), 7.53-7.45 (m, 4H), 7.32 (dd, J=10.3, 5.7 Hz, 1H), 7.26 (d, J=8.2 Hz, 2H), 3.73 (t, J=6.0 Hz, 2H), 3.52 (t, J=5.7 Hz, 2H), 1.90 (quintet, J=6.3 Hz, 2H; ESI MS m/z 470 [C$_{24}$H$_{19}$F$_4$N$_5$O+H]$^+$.

EXAMPLE 34

Preparation of 8-[3-(2-Fluoro 1-oxy-pyridin-3-yl)-phenyl]-8-(4-trifluoromethoxyphenyl)-2,3,4,8-tetrahydro-imidazo[1,5-a]pyrimidin-6-ylamine

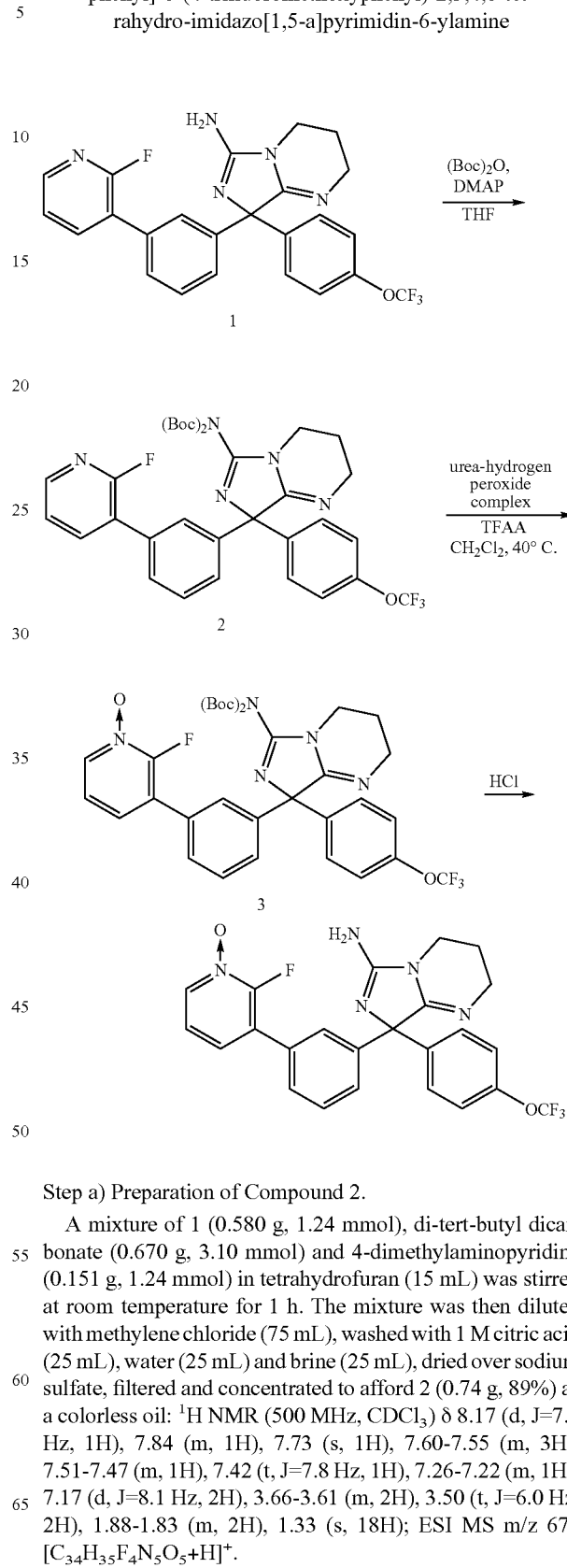

Step a) Preparation of Compound 2.

A mixture of 1 (0.580 g, 1.24 mmol), di-tert-butyl dicarbonate (0.670 g, 3.10 mmol) and 4-dimethylaminopyridine (0.151 g, 1.24 mmol) in tetrahydrofuran (15 mL) was stirred at room temperature for 1 h. The mixture was then diluted with methylene chloride (75 mL), washed with 1 M citric acid (25 mL), water (25 mL) and brine (25 mL), dried over sodium sulfate, filtered and concentrated to afford 2 (0.74 g, 89%) as a colorless oil: $^1$H NMR (500 MHz, CDCl$_3$) δ 8.17 (d, J=7.1 Hz, 1H), 7.84 (m, 1H), 7.73 (s, 1H), 7.60-7.55 (m, 3H), 7.51-7.47 (m, 1H), 7.42 (t, J=7.8 Hz, 1H), 7.26-7.22 (m, 1H), 7.17 (d, J=8.1 Hz, 2H), 3.66-3.61 (m, 2H), 3.50 (t, J=6.0 Hz, 2H), 1.88-1.83 (m, 2H), 1.33 (s, 18H); ESI MS m/z 670 [C$_{34}$H$_{35}$F$_4$N$_5$O$_5$+H]$^+$.

Step b) Preparation of Compound 3.

Trifluoroacetic anhydride (0.365 g, 1.74 mmol) was added dropwise to a stirred suspension of urea-hydrogen peroxide complex (0.169 g, 1.80 mmol) in methylene chloride (15 mL) at 0° C. The mixture was stirred for 5 min and then a solution of 2 (0.200 g, 0.29 mmol) in methylene chloride (10 mL) was added dropwise. The reaction was warmed to room temperature and then heated at 40° C. for 45 min. After this time, the reaction was cooled to room temperature, diluted with methylene chloride (50 mL) and washed with saturated aqueous sodium bicarbonate (2×20 mL) and brine (20 mL), dried over sodium sulfate, filtered and concentrated. Purification by flash chromatography (silica, 97.5:2.5 to 95:5 methylene chloride/methanol) afforded 3 (0.086 g, 41%) as a colorless oil: $^1$H NMR (300 MHz, CDCl$_3$) δ 8.25 (dt, J=6.3, 1.5 Hz, 1H), 7.73 (s, 1H), 7.68-7.62 (m, 1H), 7.57 (d, J=6.9 Hz, 2H), 7.49-7.43 (m, 2H), 7.40-7.33 (m, 1H), 7.20-7.13 (m, 3H), 3.64 (t, J=5.4 Hz, 2H), 3.50 (t, J=5.8 Hz, 2H), 1.90-1.81 (m, 2H), 1.45 (s, 18H); ESI MS m/z 686 $[C_{34}H_{35}F_4N_5O_6+H]^+$.

Step c Preparation of 8-[3-(2-Fluoro 1-oxy-pyridin-3-yl)-phenyl]-8-(4-trifluoromethoxy-phenyl)-2,3,4,8-tetrahydro-imidazo[1,5-a]pyrimidin-6-ylamine A mixture of 3 (0.08 g, 0.11 mmol) and 4 M HCl/dioxane (5 mL) was stirred at room temperature for 20 h. The solvents were evaporated and the residue diluted with saturated aqueous sodium bicarbonate (15 mL) and methylene chloride (20 mL). The layers were separated and the organic layer washed with brine (10 mL), dried over sodium sulfate, filtered and concentrated. The crude product was purified by preparative HPLC. The appropriate fractions were combined, concentrated, then neutralized with saturated aqueous sodium bicarbonate (10 mL) and extracted with methylene chloride (3×10 mL). The combined organic layers were washed with brine (10 mL), dried over sodium sulfate, filtered and concentrated. The residue was freeze dried from acetonitrile/water (8 mL, 1:1) to afford the title product as a white solid, 0.018 g (32% yield), $^1$H NMR (300 MHz, CDCl$_3$) δ 8.24 (dt, J=6.3, 1.6 Hz, 1H), 7.74 (s, 1H), 7.62-7.53 (m, 3H), 7.48-7.32 (m, 3H), 7.20-7.12 (m, 3H), 3.66 (t, J=5.9 Hz, 2H), 3.60 (t, J=5.5 Hz, 2H), 1.88 (t, J=5.7 Hz, 2H); ESI MS m/z 486 $[C_{24}H_{19}F_4N_5O_2+H]^+$.

EXAMPLE 35

Preparation of 7-[3-(2-Fluoro-pyridin-3-yl)-phenyl]-7-(4-trifluoromethoxy-phenyl)-2,7-dihydro-3H-imidazo[1,5-a]imidazol-5-ylamine

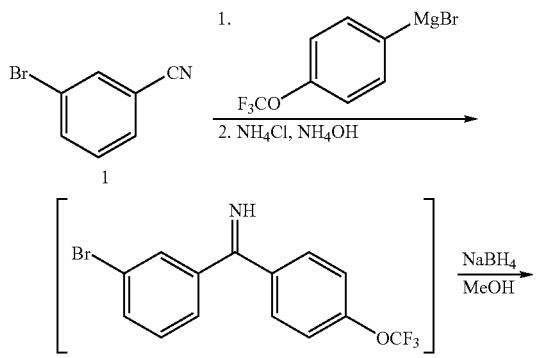

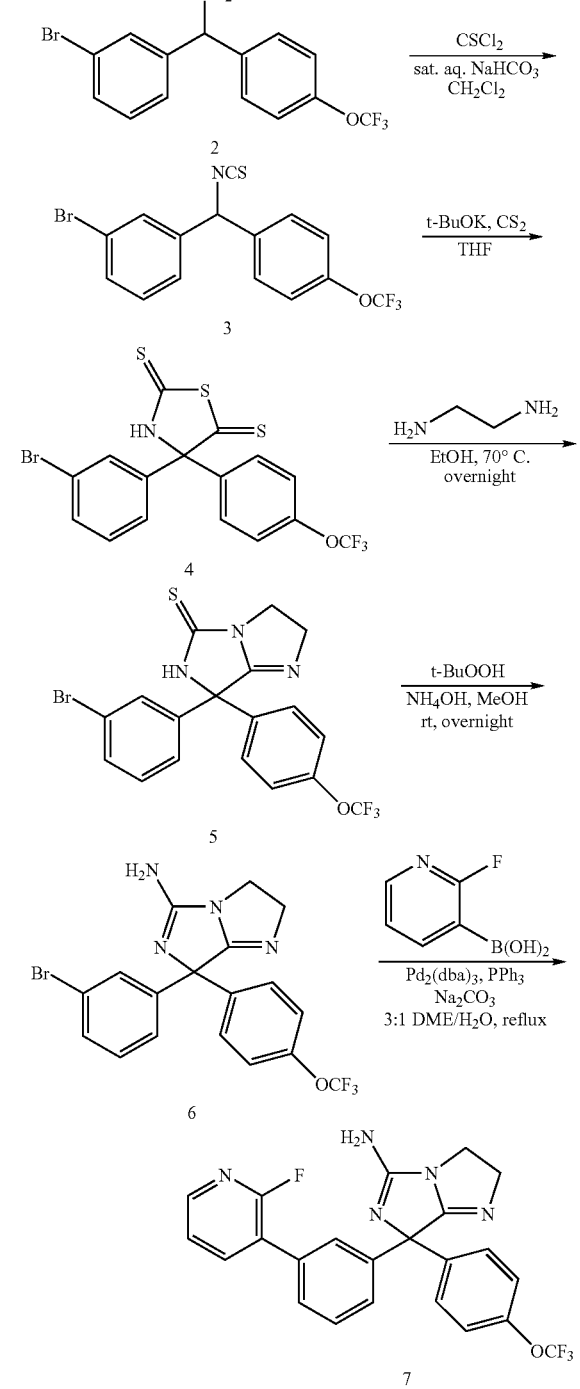

Step a) Preparation of Compound 2.

A mixture of magnesium (0.60 g, 24.7 mmol) in THF (6 mL) was heated to 50° C. and treated dropwise with a solution of 1-bromo-4-(trifluoromethoxy)-benzene (5.96 g, 24.7 mmol) in THF (18 mL) over a period of 10 min. After stirring at 50° C. for an additional 1.5 h, the mixture was cooled to room temperature and treated with a solution of 1 (3.0 g, 16.5 mmol) in THF (12 mL). The mixture was then reheated to 65° C. for 1 h. After this time, the reaction mixture was cooled to room temperature and poured onto a solution of saturated aqueous ammonium chloride (20 mL) and conc. ammonium hydroxide (20 mL) at −15° C. and stirred for 5 min. This mixture was then filtered through a pad of celite 521 with ether (100 mL). The organic layer in the filtrate was separated, washed with brine (50 mL), dried over magnesium sulfate, filtered and concentrated to afford the crude imine (3.90 g, 68%) as an amber oil. A solution of this crude imine (3.90 g, 11.3 mmol) in MeOH (20 mL) was cooled with an ice bath and treated with sodium borohydride (0.86 g, 22.7 mmol). The cooling bath was removed and the mixture stirred at room temperature for 3 h. After this time the mixture was concentrated and partitioned between 1 N NaOH (100 mL) and methylene chloride (100 mL). The organic layer was separated and washed with brine (100 mL), dried over potassium carbonate, filtered and concentrated. Purification by flash chromatography (silica, 1:4 ethyl acetate/hexanes) afforded 2 (1.98 g, 34% over 2 steps): $^1$H NMR (300 MHz, CDCl$_3$) δ 7.56 (t, J=1.7 Hz, 1H), 7.40-7.15 (m, 7H), 5.19 (s, 1H); ESI MS m/z 329 [C$_{18}$H$_{15}$BrF$_4$N$_2$O$_2$—NH$_2$+H]$^+$.

Step b) Preparation of Compound 3

A mixture of 2 (0.66 g, 1.91 mmol) in methylene chloride (2 mL) and saturated aqueous sodium bicarbonate (2 mL) was cooled with an ice bath, treated with thiophosgene (0.24 g, 2.10 mmol) and stirred vigorously for 30 min. The organic layer was separated, washed with brine (2 mL), dried over sodium sulfate and concentrated to afford 3 (0.74 g, 100%) as a yellow oil: $^1$H NMR (300 MHz, CDCl$_3$) δ 7.49-7.22 (m, 8H), 5.97 (s, 1H).

Step c) Preparation of Compound 4

To a mixture of potassium t-butoxide (0.070 g, 0.623 mmol) in tetrahydrofuran (2 mL) at −78° C. was added dropwise a solution of 3 (0.220 g, 0.567 mmol) and carbon disulfide (0.065 g, 0.850 mmol) in tetrahydrofuran (3 mL). The reaction was stirred at −78° C. for 0.5 h, then warmed to room temperature slowly and stirred overnight at room temperature. The reaction was then diluted with ethyl acetate (50 mL) and water (10 mL). The organic layer was separated, washed with brine (10 mL), dried over sodium sulfate and concentrated, to afford 4 (0.26 g, 99%) as a clear oil: $^1$H NMR (300 MHz, CDCl$_3$) δ 7.86-7.10 (m, 8H), 3.70 (s, br, 1H).

Step d) Preparation of Compound 5

A solution of 4 (0.850 g, 1.83 mmol) and ethylenediamine (0.330 g, 5.49 mmol) in ethanol (15 mL) was heated overnight at 70° C. The reaction was cooled to room temperature and concentrated. Purification by flash chromatography (silica, 1:4 ethyl acetate/hexanes) afforded 5 (0.45 g, 54%) as a white solid: $^1$H NMR (300 MHz, CDCl$_3$) δ 8.50 (s, 1H), 7.59-7.19 (m, 8H), 4.46 (t, J=8.5 Hz, 2H), 3.87 (t, J=8.5 Hz, 2H); ESI MS m/z 456 [C$_{18}$H$_{13}$BrF$_3$N$_3$OS+H]$^+$.

Step e) Preparation of Compound 6

A mixture of 5 (0.200 g, 0.438 mmol) and t-butyl hydroperoxide (0.79 g of a 70% solution in water, 8.80 mmol) in methanol (20 mL) and concentrated aqueous ammonium hydroxide (4 mL) was stirred overnight at room temperature. The reaction was then concentrated. Purification by flash chromatography (silica, 95:5:0.25 methylene chloride/methanol/concentrated ammonium hydroxide) afforded 6 (0.156 g, 81%) as a white solid: $^1$H NMR (300 MHz, CD$_3$OD) δ 7.58 (t, J=1.5 Hz, 1H), 7.49-7.44 (m, 3H), 7.36 (dt, J=7.8, 1.5 Hz, 1H), 7.29-7.23 (m, 3H), 4.41 (t, J=8.7 Hz, 2H), 3.75 (t, J=8.7 Hz, 2H); ESI MS m/z 440 [C$_{18}$H$_{14}$BrF$_3$N$_4$O+H]$^+$.

Step f) Preparation of 7-[3-(2-fluoro-pyridin-3-yl)-phenyl]-7-(4-trifluoromethoxyphenyl)-2,7-dihydro-3H-imidazo[1,5-a]imidazol-5-ylamine A mixture of 6 (0.070 g, 0.159 mmol), triphenylphosphine (0.004 g, 0.016 mmol), bis(dibenzylideneacetone)palladium (0) (0.007 g, 0.008 mmol), sodium carbonate (0.051 g, 0.478 mmol) and 2-fluoro-3-boronic acid (0.040 g, 0.287 mmol) in ethylene glycol dimethyl ether (6 mL) and water (2 mL) was degassed and heated at 80° C. for 2.5 h. The mixture was cooled to room temperature and diluted with ethyl acetate (100 mL) and water (50 mL). The organic layer was separated, washed with brine (20 mL), dried over sodium sulfate, filtered, and concentrated. Purification by flash chromatography (silica, 93:7:0.25 methylene chloride/methanol/concentrated ammonium hydroxide) and then by preparative HPLC afforded a mixture of starting material and product. A mixture of this material (0.032 g, 0.073 mmol), triphenylphosphine (0.002 g, 0.007 mmol), bis(dibenzylideneacetone)palladium (0) (0.003 g, 0.004 mmol), sodium carbonate (0.023 g, 0.220 mmol) and 2-fluoro-3-boronic acid (0.019 g, 0.131 mmol) in ethylene glycol dimethyl ether (6 mL) and water (2 mL) was degassed and heated at 80° C. overnight. The organic layer was separated, washed with brine (20 mL), dried over sodium sulfate, filtered, and concentrated. Purification by flash chromatography (silica, 95:5:0.25 methylene chloride/methanol/concentrated ammonium hydroxide) afforded the title product as a white solid, 0.030 g (41% yield), mp 95-100° C.; $^1$H NMR (500 MHz, CD$_3$OD) 8.17 (dt, J=4.5, 1.0 Hz, 1H), 8.02 (ddd, J=7.5, 2.0, 2.0 Hz, 1H), 7.64-7.38 (m, 9H), 7.26 (d, J=8.0 Hz, 2H), 4.43 (d, J=9.0 Hz, 2H), 3.78 (d, J=9.0 Hz, 2H); IR (ATR) 2925, 1644, 1601, 1504, 1450, 1434, 1400, 1250, 1211, 1157, 1010, 966, 791 cm$^{-1}$; ESI MS m/z 456 [C$_{23}$H$_{17}$F$_4$N$_5$O+H]$^+$.

EXAMPLE 36

Preparation of 9-[3-(2-Fluoro-pyridin-3-yl)-phenyl]-9-(4-trifluoromethoxyphenyl)-2,4,5,9-tetrahydro-3H-imidazo[1,5-a][1,3]diazepin-7-ylamine

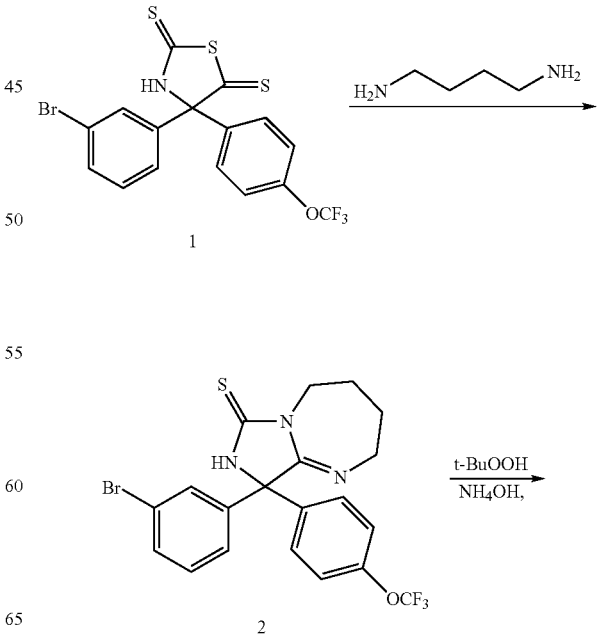

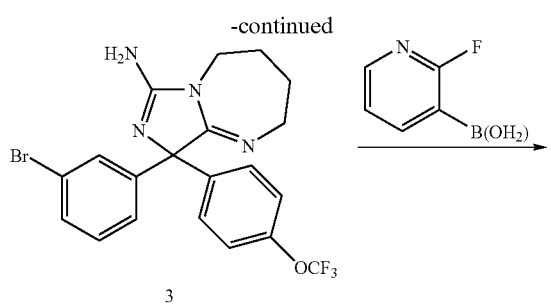

Step a) Preparation of Compound 2.

A solution of 1 (0.50 g, 1.08 mmol) and 1,4-diamino propane (0.28 g, 3.23 mmol) in ethanol was heated at 70° C. for 18 h, cooled to room temperature and concentrated in vacuo. The concentrate was partitioned between ethyl acetate and water. The organic layer was separated, washed with brine, dried over magnesium sulfate and concentrated. Purification of the resultant residue by flash chromatography (silica, 1:4 ethyl acetate/hexanes) afforded 2 (0.22 g, 42%) as a white foam: $^1$H NMR (300 MHz, CDCl$_3$) δ 7.47 (m, 2H), 7.33 (d, J=8.9 Hz, 2H), 7.25-7.18 (m, 4H), 4.15 (m, 2H), 3.81 (m, 2H), 1.99 (m, 4H); ESI MS m/z 484 [C$_{20}$H$_{17}$BrF$_3$N$_3$OS+H]$^+$.

Step b) Preparation of Compound 3

A mixture of 2 (0.22 g, 0.454 mmol) and t-butyl hyproperoxide (1.17 g of a 70% solution in water, 9.08 mmol) in methanol and concentrated aqueous ammonium hydroxide (4.4 mL) was stirred overnight at room temperature, treated with 10% aqueous sodium thiosulfate (30 mL) and concentrated to remove most of the methanol. The remaining aqueous mixture was extracted with methylene chloride. The methylene chloride extracts were combined, washed with brine, dried over magnesium sulfate, and concentrated. Purification of the resultant residue by flash chromatography (silica, 95:5:0.25 methylene chloride/methanol/concentrated ammonium hydroxide) afforded 3 (0.136 g, 65%) as a white foam: $^1$H NMR (300 MHz, CDCl$_3$) δ 7.63 (t, J=1.7 Hz, 1H), 7.46 (dd, J=6.8, 2.0 Hz, 2H), 7.39-7.33 (m, 2H), 7.19-7.12 (m, 3H), 3.73 (m, 2H), 3.57 (m, 2H), 1.93 (m, 4H); ESI MS m/z 467 [C$_{20}$H$_{18}$BrF$_3$N$_4$O+H]$^+$.

Step c) Preparation of 9-[3-(2-Fluoro-pyridin-3-yl)-phenyl]-9-(4-trifluoromethoxyphenyl)-2,4,5,9-tetrahydro-3H-imidazo[1,5-a][1,3]diazepin-7-ylamine A mixture of 3 (0.065 g, 0.139 mmol), 2-fluoropyridine-3-boronic acid (0.035 g, 0.250 mmol), bis(triphenylphosphino)palladium(II) chloride (0.0049 g, 0.007 mmol), triphenylphosphine (0.0036 g, 0.014 mmol) and sodium carbonate (0.044 g, 0.417 mmol) in 3:1 DME/water was heated at reflux temperature for 1 h, cooled to room temperature and diluted with ethyl acetate and water. The organic layer was separated, washed with brine, dried over magnesium sulfate and concentrated. Purification of the resultant residue by flash chromatography (silica, 95:5:0.25 methylene chloride/methanol/ concentrated ammonium hydroxide) afforded 0.049 g of a white foam. This material was freeze dried from 2:1 acetonitrile/water to afford the title product as a white solid, 0.041 g (62% yield), mp 88-97° C.; $^1$H NMR (500 MHz, CD$_3$OD) δ 8.16 (d, J=4.3 Hz, 1H), 8.00 (m, 1H), 7.59-7.37 (m, 7H), 7.22 (d, J=8.7 Hz, 2H), 3.73-3.64 (m, 4H), 1.96 (m, 4H); ESI MS m/z 484 [C$_{25}$H$_{21}$F$_4$N$_5$O+H]$^+$;

EXAMPLE 37

Preparation of 1-[3-(2-Fluoro-pyridin-3-yl)-phenyl]-1-(4-trifluoromethoxyphenyl)-1,4,5,6,7,8-hexahydro-2,3a,9-triaza-cyclopentacycloocten-3-ylamine

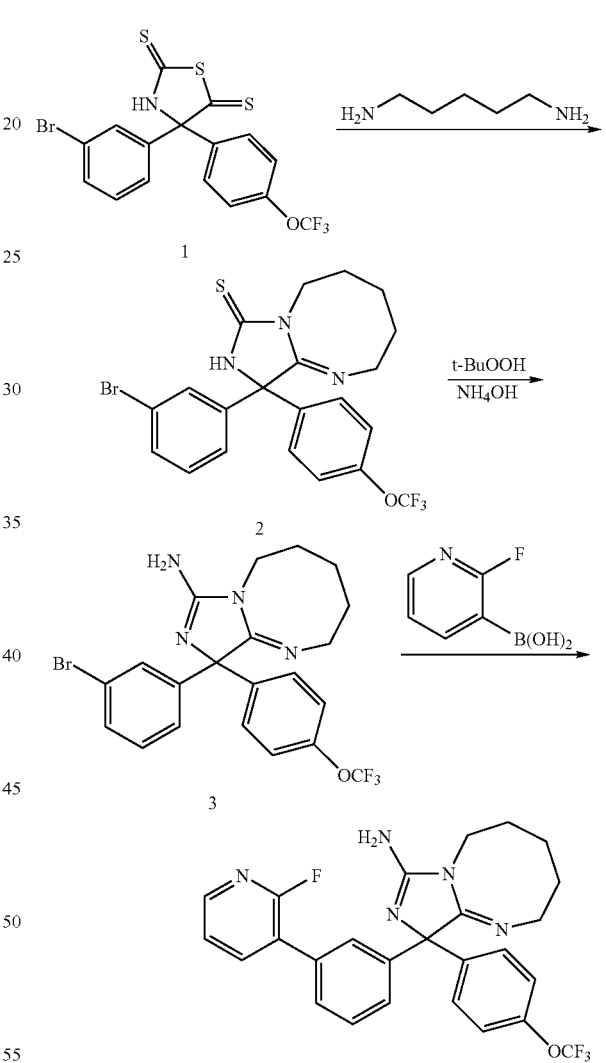

Step a) Preparation of Compound 2

A solution of 1 (0.50 g, 1.08 mmol) and 1,5-diamino pentane (0.33 g, 3.23 mmol) in ethanol was heated at 70° C. for 5 h, then at 100° C. for 17 h and finally at 120° C. for 6 h. The reaction was cooled to room temperature, concentrated and the concentrate was partitioned between ethyl acetate and water. The organic layer was separated, washed with, dried over magnesium sulfate and concentrated. Purification of the resultant residue by flash chromatography (silica, 1:4 ethyl acetate/hexanes) afforded 2 (0.153 g, 28%) as a white foam:

$^1$H NMR (300 MHz, CDCl$_3$) δ 7.54 (t, J=1.7 Hz, 1H)), 7.50-7.19 (m, 7H), 4.45 (t, J=6.6 Hz, 2H), 4.01 (t, J=6.6 Hz, 2H), 1.96-1.86 (m, 4H), 1.48-1.44 (m, 2H); ESI MS m/z 498 [C$_{21}$H$_{19}$BrF$_3$N$_3$OS+H]$^+$.

Step b) Preparation of Compound 3

A mixture of 2 (0.15 g, 0.301 mmol) and t-butyl hyperoxide (0.77 g of a 70% solution in water, 6.02 mmol) in methanol and concentrated aqueous ammonium hydroxide (3 mL) was stirred overnight at room temperature treated with 10% aqueous sodium thiosulfate (20 mL) and concentrated to remove most of the methanol. The remaining aqueous mixture was extracted with methylene chloride. The methylene chloride extracts were combined, washed with brine, dried over magnesium sulfate and concentrated. Purification of the resultant residue by flash chromatography (silica, 95:5:0.25 methylene chloride/methanol/concentrated ammonium hydroxide) afforded 3 (0.073 g, 52%) as a white foam: $^1$H NMR (300 MHz, CDCl$_3$) δ 7.63 (t, J=1.8 Hz, 1H), 7.49 (dd, J=6.8, 2.0 Hz, 2H), 7.49-7.37 (m, 2H), 7.20-7.13 (m, 3H), 3.96 (m, 4H), 1.90 (m, 4H), 1.56 (m, 2H); ESI MS m/z 482 [C$_{21}$H$_{20}$BrF$_3$N$_4$O+H]$^+$.

Step c) Preparation of 1-[3-(2-Fluoro-pyridin-3-yl)-phenyl]-1-(4-trifluoromethoxyphenyl)-1,4,5,6,7,8-hexahydro-2,3a,9-triaza-cyclopentacycloocten-3-ylamine A mixture of 3 (0.065 g, 0.135 mmol), 2-fluoropyridine-3-boronic acid (0.034 g, 0.243 mmol), bis(triphenylphosphino)palladium(II) chloride (0.0047 g, 0.0068 mmol), triphenylphosphine (0.0035 g, 0.014 mmol) and sodium carbonate (0.043 g, 0.405 mmol) in 3:1 DME/water (2.0 mL) was heated at reflux temperature for 1.5 h, cooled to room temperature and diluted with ethyl acetate and water. The organic layer was separated, washed with brine, dried over magnesium sulfate and concentrated. Purification of the resultant residue by flash chromatography (silica, 97:3:0.25 methylene chloride/methanol/concentrated ammonium hydroxide) afforded 0.041 g of a white foam. This material was freeze dried from 2:1 acetonitrile/water to afford the title product as a white solid, 0.033 g (49% yield), mp 95-99° C.; $^1$H NMR (500 MHz, CD$_3$OD) δ 8.16 (m, 1H), 8.00 (m, 1H), 7.62 (d, J=1.4 Hz, 1H), 7.55-7.37 (m, 6H), 7.23 (d, J=8.1 Hz, 2H), 4.07 (m, 2H), 3.96-3.89 (m, 2H), 1.93-1.82 (m, 4H), 1.55 (m, 2H); IR (ATR) 1649, 1433, 1251, 1214, 1155 cm$^{-1}$; ESI MS m/z 498 [C$_{26}$H$_{23}$F$_4$N$_5$O+H]$^+$.

EXAMPLE 38

Preparation of 8-[3-(2-Fluoro-pyridin-3-yl)-phenyl]-8-(4-methoxymethoxyphenyl)-2,3,4,8-tetrahydro-imidazo[1,5-a]pyrimidin-6-ylamine

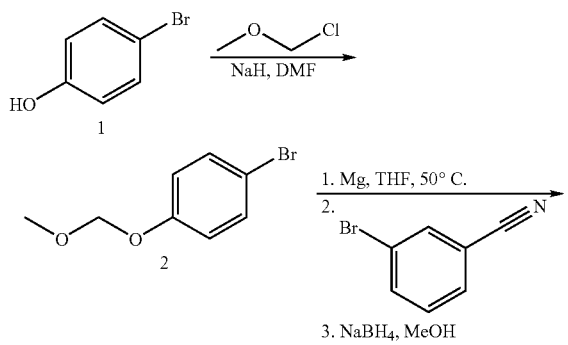

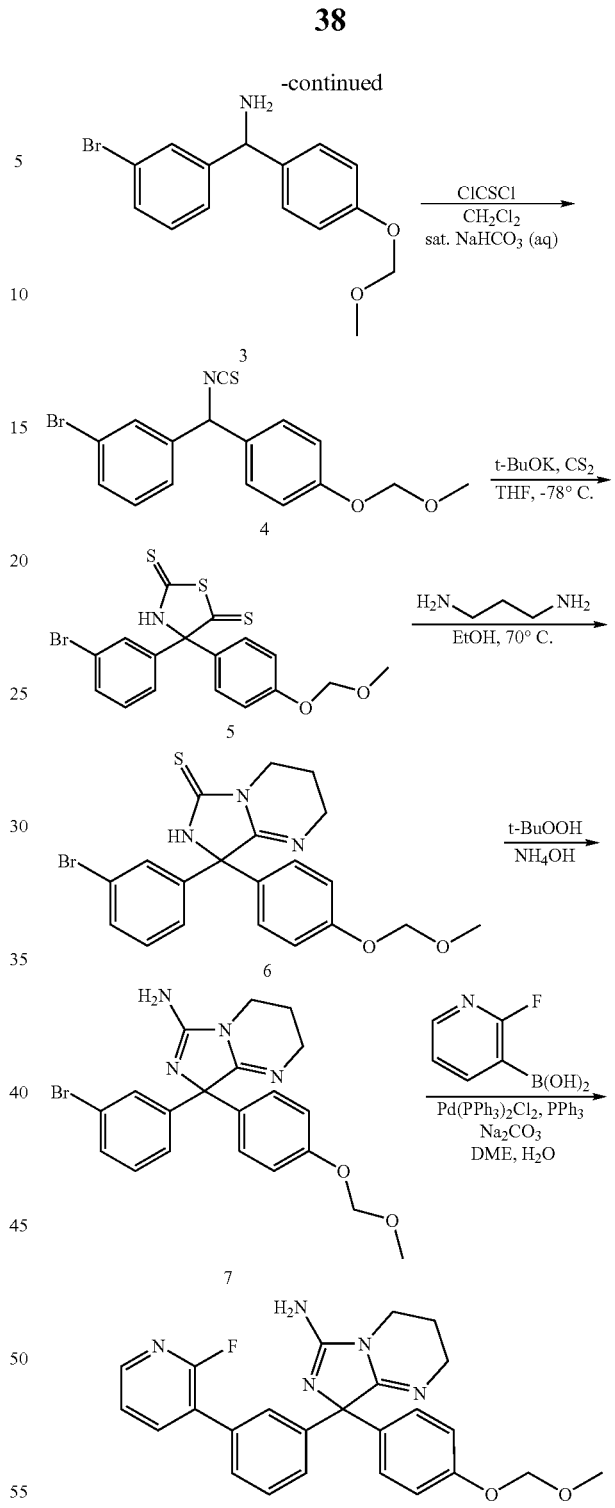

Step a) Preparation of Compound 2

A mixture of 4-bromophenol (4.00 g, 23.1 mmol) in acetonitrile (100 mL) at 0° C. was treated portionwise with sodium hydride (1.10 g of a 60% dispersion in oil, 27.7 mmol). The mixture was stirred for 5 min, then warmed to room temperature and stirred for an additional 15 min. Chloromethyl methyl ether (2.23 g, 27.7 mmol) was added dropwise and the mixture stirred for 20 min. The solvents were evaporated and the residue partitioned between ethyl acetate and water. The layers were separated and the organic layer washed with brine, dried over sodium sulfate, filtered and concentrated to afford 2 (5.30 g, 106%) as a colorless oil: $^1$H NMR (500 MHz, CDCl$_3$) δ 7.38 (d, J=8.9 Hz, 2H), 6.92 (d, J=8.9 Hz, 2H), 5.14 (s, 2H), 3.46 (s, 3H).

Step b) Preparation of Compound 3

A small crystal of iodine was added to a stirred mixture of magnesium (0.197 g, 8.20 mmol) in tetrahydrofuran and then heated to 50° C. A solution of 2 (1.78 g, 8.20 mmol) in tetrahydrofuran was added dropwise and the mixture stirred for 45 min. The mixture was cooled to room temperature and a solution of 3-bromobenzonitrile (1.00 g, 5.49 mmol) in tetrahydrofuran was slowly added. The mixture was then heated at 65° C. for 16 h. The reaction was cooled to room temperature, anhydrous methanol was added and the mixture stirred for 45 min. The mixture was cooled to 0° C. and sodium borohydride (0.415 g, 10.98 mmol) was added portionwise. The cooling bath was removed and the mixture stirred for 3 hr. Saturated ammonium chloride (10 mL) was added, most of the methanol and THF was removed under reduced pressure. The remaining aqueous residue was extracted with methylene chloride. The combined organic layers were dried over sodium sulfate and concentrated. Purification of the resultant residue by flash chromatography (silica, 4:1 to 1:1 hexanes/ethyl acetate) afforded 3 (0.89 g, 50%) as a colorless oil: $^1$H NMR (300 MHz, CDCl$_3$) δ 7.55 (br s, 1H), 7.39-7.23 (m, 4H), 7.15 (t, J=7.8 Hz, 1H), 6.98 (d, J=8.7 Hz, 2H, 5.15 (s, 2H), 5.14 (s, 1H), 3.46 (s, 3H); ESI MS m/z 305 [(C$_{15}$H$_{16}$BrNO$_2$—NH$_2$)+H]$^+$.

Step c) Preparation of Compound 4

A mixture of 3 (0.89 g, 2.76 mmol) in methylene chloride and saturated aqueous sodium bicarbonate was cooled with an ice bath, treated with thiophosgene (0.35 g, 3.03 mmol) and stirred vigorously for 40 min. The phases were separated and the aqueous phase was extracted with methylene chloride. The combined organic phases were washed with brine, dried over sodium sulfate and concentrated to afford 4 (0.80 g, 80%) as a yellow oil: $^1$H NMR (300 MHz, CDCl$_3$) δ 7.47-7.42 (m, 2H), 7.28-7.18 (m, 4H), 7.04 (d, J=8.8 Hz, 2H), 5.92 (s, 1H), 5.17 (s, 2H), 3.46 (s, 3H).

Step d) Preparation of Compound 5

To a mixture of potassium t-butoxide (0.27 g, 2.41 mmol) in tetrahydrofuran at −78° C. was added dropwise a solution of 4 (0.80 g, 0.2.19 mmol) and carbon disulfide (0.25 g, 3.28 mmol) in tetrahydrofuran. The reaction was stirred at −78° C. for 0.5 h, then warmed to room temperature slowly and stirred for 1.5 h at room temperature. After this time, TLC analysis indicated that the reaction was not complete, so the mixture was cooled to −78° C. and carbon disulfide (0.06 g, 0.83 mmol) was added followed by a solution of potassium t-butoxide (0.05 g, 0.44 mmol) in tetrahydrofuran. The reaction was stirred at −78° C. for 30 min, then warmed to room temperature and stirred for 45 min. The reaction was then diluted with ethyl acetate and water and brine. The organic layer was separated, and the aqueous layer was extracted with ethyl acetate. The combined organic layers were washed with brine, dried over sodium sulfate and concentrated, to afford 5 (1.1 g, 115%) as a red semi-solid: $^1$H NMR (300 MHz, CDCl$_3$) δ 7.48 (t, J=1.8 Hz, 1H), 7.43 (d, J=7.8 Hz, 1H), 7.30-7.25 (m, 1H), 7.20 (d, J=8.8 Hz, 2H), 7.14 (t, J=7.9 Hz, 1H), 6.94 (d, J=8.8 Hz, 2H), 5.11 (s, 2H), 3.42 (s, 3H).

Step e) Preparation of Compound 6.

A mixture of 5 (1.10 g, 2.18 mmol) and 1,3-diaminopropane (0.484 g, 6.54 mmol) in ethanol was heated at 70° C. for 1 h, cooled to room temperature and concentrated in vacuo. The resultant residue was diluted with ethyl acetate, washed sequentially with water and brine, dried over sodium sulfate and concentrated. Purification of this residue by flash chromatography (silica, 4:1 to 3:1 hexanes/ethyl acetate) afforded 6 (0.70 g, 72%) as a colorless oil: $^1$H NMR (300 MHz, CDCl$_3$) δ 7.53 (t, J=1.7 Hz, 1H), 7.47 (dt, J=7.7, 1.4 Hz, 1H), 7.30-7.17 (m, 3H), 7.06-6.97 (m, 3H), 5.17 (s, 2H), 3.89 (t, J=6.0 Hz, 2H), 3.50 (t, J=5.5 Hz, 2H), 3.47 (s, 3H), 1.91 (t, J=5.4 Hz, 2H); ESI MS m/z 446 [C$_{20}$H$_{20}$BrN$_3$O$_2$S+H]$^+$.

Step f) Preparation of Compound 7.

A mixture of 6 (0.630 g, 1.40 mmol) and t-butyl hydroperoxide (3.6 g of a 70% solution in water, 28 mmol) in methanol and concentrated aqueous ammonium hydroxide (18 mL) was stirred at room temperature for 24 h, treated with 10% aqueous sodium thiosulfate (10 mL) and concentrated to remove most of the methanol. The remaining aqueous mixture was extracted with methylene chloride. The methylene chloride extracts were combined, washed sequentially with water and brine, dried over sodium sulfate and concentrated. Purification of this residue by flash chromatography (silica, 95:5:0.25 methylene chloride/methanol/concentrated ammonium hydroxide) afforded 7 (0.400 g, 67%) as an off-white solid: $^1$H NMR (300 MHz, CDCl$_3$) δ 7.66 (t, J=1.8 Hz, 1H), 7.40-7.32 (m, 4H), 7.16 (t, J=7.9 Hz, 1H), 6.97 (d, J=8.9 Hz, 2H), 5.15 (s, 2H), 3.62-3.55 (m, 4H), 3.45 (s, 3H), 1.86 (t, J=5.5 Hz, 2H); ESI MS m/z 429 [C$_{20}$H$_{21}$BrN$_4$O$_2$+H]$^+$.

Step g) Preparation of 8-[3-(2-Fluoro-pyridin-3-yl)-phenyl]-8-(4-methoxymethoxyphenyl)-2,3,4,8-tetrahydro-imidazo[1,5-a]pyrimidin-6-ylamine A mixture of 7 (0.370 g, 0.860 mmol), 2-fluoropyridine-3-boronic acid (0.243 g, 1.72 mmol), bis(triphenylphosphino)palladium(II) chloride (0.030 g, 0.043 mmol), triphenylphosphine (0.022 g, 0.086 mmol) and sodium carbonate (0.273 g, 2.58 mmol) in 3:1 DME/water (16 mL) was heated at 80° C. for 1 h, cooled to room temperature and diluted with ethyl acetate and water. The organic layer was separated, washed with brine, dried over sodium sulfate and concentrated. Purification of the resultant residue by flash chromatography (silica, 96:4:0.25 methylene chloride/methanol/concentrated ammonium hydroxide) afforded a pale yellow solid, 0.300 g (78% yield). A 0.030 g sample of this solid was dissolved in acetonitrile and water and freeze dried to afford the title product as an off-white-solid, 0.023 g, mp 95-105° C.; $^1$H NMR (300 MHz, CDCl$_3$) δ 8.16 (dt, J=5.0, 1.7 Hz, 1H), 7.88-7.80 (m, 1H), 7.71-7.67 (m, 1H), 7.53-7.44 (m, 2H), 7.41 (d, J=7.6 Hz, 1H), 7.37 (d, J=8.8 Hz, 2H), 7.27-7.20 (m, 1H), 6.97 (d, J=8.8 Hz, 2H), 5.15 (s, 2H), 3.68-3.54 (m, 4H), 3.45 (s, 3H), 1.85 (t, J=5.6 Hz, 2H); ESI MS m/z 446 [C$_{25}$H$_{24}$FN$_5$O$_2$+H]$^+$.

EXAMPLE 39

Preparation of 8-(2,3-Dihydro-benzo[1,4]dioxin-6-yl)-8-[3-(2-fluoro-pyridin-3-yl)phenyl]-2,3,4,8-tetrahydro-imidazo[1,5-a]pyrimidin-6-ylamine

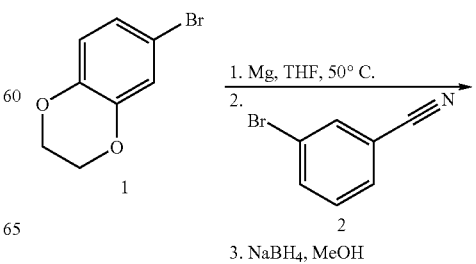

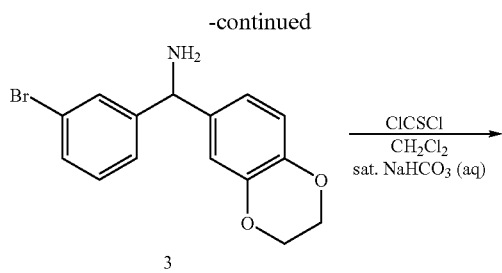
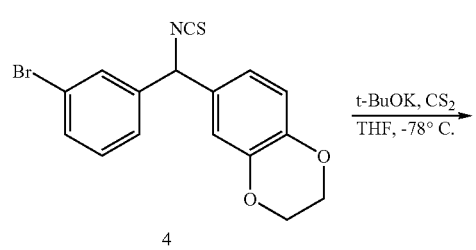
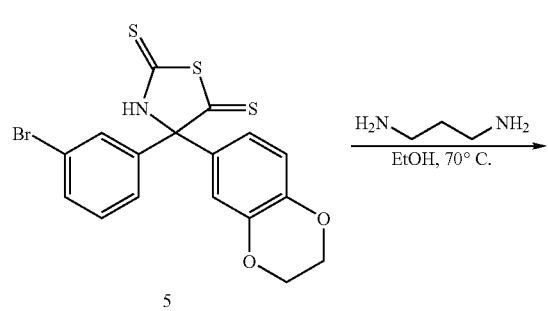
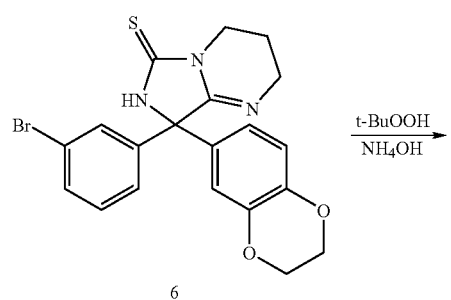
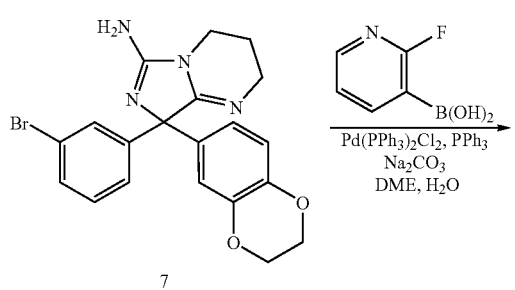
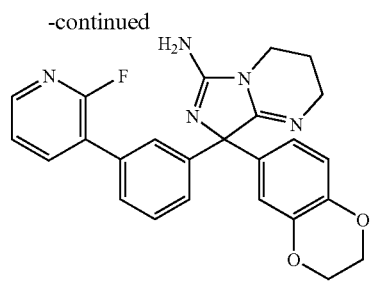
Using essentially the same procedures described in Example 38, steps a-g, and employing compound 1 as starting material, the title product was obtained as an off-white solid, mp 125-140° C.; $^1$H NMR (300 MHz, CDCl$_3$) δ 8.16 (m, 1H), 7.87-7.80 (m, 1H), 7.72 (d, J=1.4 Hz, 1H), 7.56-7.37 (m, 3H), 7.25-7.21 (m, 1H), 6.98 (d, J=2.1 Hz, 1H), 6.89-6.77 (m, 2H), 4.22 (s, 4H), 3.62-3.55 (m, 4H), 2.95 (br s, 2H), 1.88-1.84 (m, 2H); ESI MS m/z 444 $[C_{25}H_{22}FN_5O_2+H]^+$.
EXAMPLE 40
Preparation of 8-Benzo[3]dioxol-5-yl-8-[3-(2-fluoro-pyridin-3-yl)-phenyl]-2,3,4,8-tetrahydro-imidazo[1,5-a]pyrimidin-6-ylamine
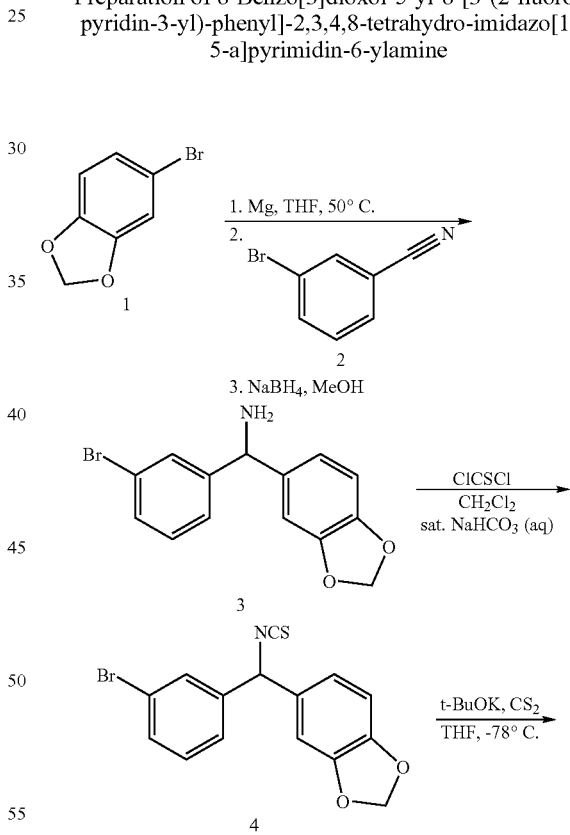
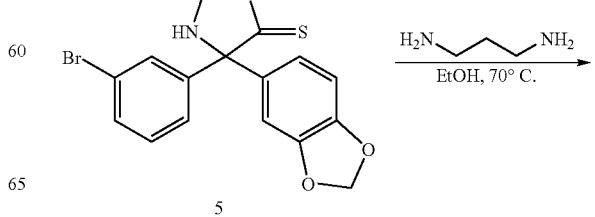

-continued

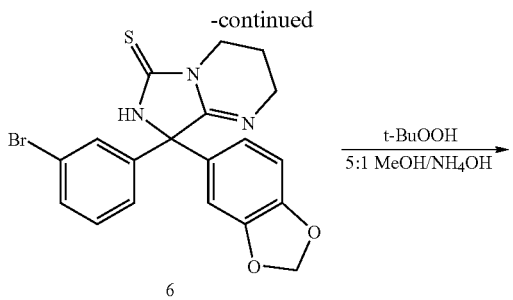

6

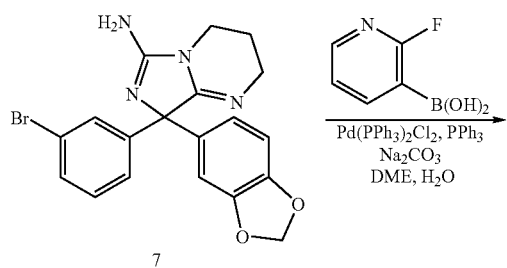

7

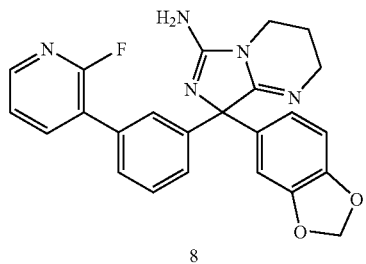

8

Using essentially the same procedures described in Example 38, steps a-g, and employing compound 1 as starting material, the title product was obtained as an off-white solid, mp 106-119° C.; $^1$H NMR (300 MHz, CD$_3$OD) δ 8.17-8.14 (m, 1H), 8.04-7.98 (m, 1H), 7.56 (d, J=1.2 Hz, 1H), 7.53-7.36 (m, 4H), 6.87 (dd, J=8.2, 1.8 Hz, 1H), 6.81 (d, J=1.7 Hz, 1H), 6.75 (d, J=8.2 Hz, 1H), 5.92 (s, 2H), 3.68 (t, J=5.9 Hz, 2H), 3.47 (t, J=5.4 Hz, 2H), 1.88-1.84 (m, 2H); ESI MS m/z 430 [C$_{24}$H$_{20}$FN$_5$O$_2$+H]$^+$.

EXAMPLE 41

Preparation of 8-(4-Difluoromethoxyphenyl)-8-[3-(2-fluoropyridin-3-yl)phenyl]-2,3,4,8-tetrahydroimidazo[1,5-a]pyrimidin-6-ylamine

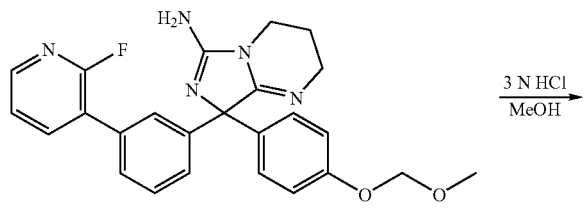

-continued

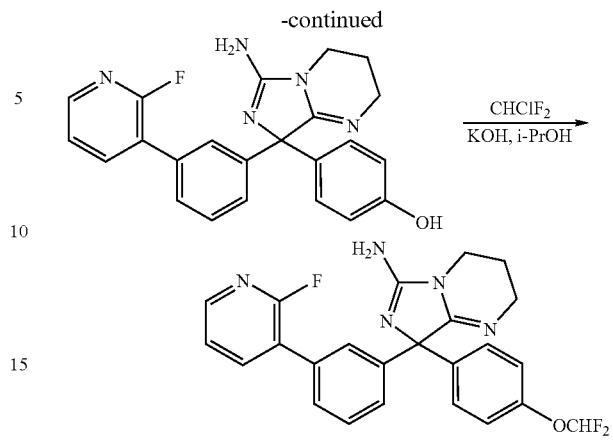

A mixture of 8-[3-(2-fluoropyridin-3-yl)phenyl]-8-(4-methoxymethoxyphenyl)-2,3,4,8-tetrahydroimidazo[1,5-a]pyrimidin-6-ylamine (1.10 g, 2.46 mmol) and 3 N hydrochloric acid (60 mL) in methanol was stirred at room temperature for 16 h, neutralized with aqueous sodium hydroxide and concentrated in vacuo. The residue obtained was triturated with ethanol, the solids removed by filtration and the filtrate concentrated. Purification of the concentrate by flash chromatography (silica, 90:10 methylene chloride/methanol) afforded a white solid (0.70 g, 70%). A 0.040 g sample of this solid was further purified by semi-preparative liquid chromatography to afford 4-{6-amino-8-[3-(2-fluoro-pyridin-3-yl)-phenyl]-2,3,4,8-tetrahydro-imidazo[1,5-a]pyrimidin-8-yl}-phenol as a white solid (0.0073 g), mp 164-181° C.; $^1$H NMR (500 MHz, CD$_3$OD) δ 8.15 (d, J=5.0 Hz, 1H), 8.03-7.97 (m, 1H), 7.57 (br s, 1H), 7.54-7.48 (m, 1H), 7.46-7.41 (m, 2H), 7.40-7.36 (m, 1H), 7.16 (d, J=8.7 Hz, 2H), 6.73 (d, J=8.7 Hz, 2H), 3.69 (t, J=6.0 Hz, 2H), 3.50-3.44 (m, 2H), 1.90-1.83 (m, 2H); ESI MS m/z 402 [C$_{23}$H$_{20}$FN$_5$O+H]$^+$.

A mixture of 4-{6-amino-8-[3-(2-fluoro-pyridin-3-yl)-phenyl]-2,3,4,8-tetrahydroimidazo[1,5-a]pyrimidin-8-yl}-phenol (0.285 g, 0.710 mmol) and potassium hydroxide (0.396 g, 7.10 mmol) in 2-propanol was stirred for 10 min at room temperature, cooled to −45° C., bubbled with FREON 22 (6.7 g, 77.0 mmol) and sealed. The sealed reaction mixture was warmed to room temperature, gradually warmed to 50° C., stirred for 90 min at 50° C., cooled to room temperature, unsealed and quenched by carefully adding the reaction mixture to water. The aqueous mixture was diluted with methylene chloride and the layers separated. The organic layer was washed with brine, dried over sodium sulfate and concentrated. Purification of this residue by flash chromatography (silica, 95:5:0.25 methylene chloride/methanol/concentrated ammonium hydroxide) afforded an off-white solid (0.055 g, 17%). This solid was further purified by semi-preparative LC to afford the title product as a white solid, (0.033 g), mp 104-114° C.; $^1$H NMR (500 MHz, CDCl$_3$) δ 8.16 (dt, J=4.7, 1.3 Hz, 1H), 7.85-7.80 (m, 1H), 7.69 (d, J=1.4 Hz, 1H), 7.53-7.45 (m, 4H), 7.40 (t, J=7.7 Hz, 1H), 7.25-7.21 (m, 1H), 7.05 (d, J=8.7 Hz, 2H), 6.47 (t, J=74.0 Hz, 1H), 3.63-3.55 (m, 4H), 1.91-1.84 (m, 2H); ESI MS m/z 452 [C$_{24}$H$_{20}$F$_3$N$_5$O+H]$^+$.

EXAMPLE 42

Preparation of 7-[3-(2-Fluoropyridin-3-yl)phenyl]-2,2-dimethyl-7-(4-trifluoromethoxyphenyl)-2,7-dihydro-3H-imidazo[1,5-a]imidazol-5-ylamine

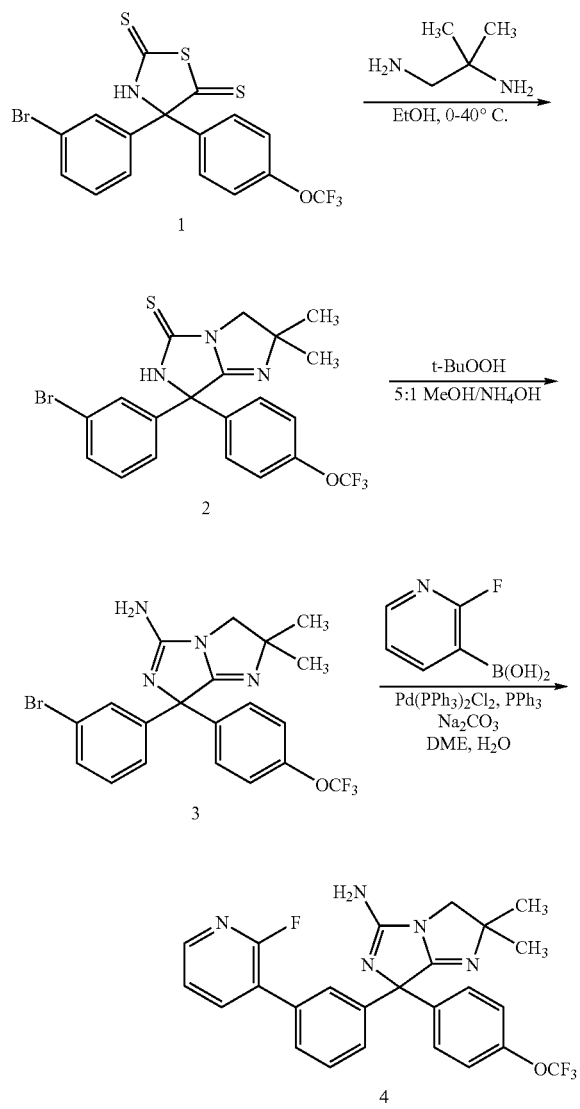

Step a) Preparation of Compound 2

A solution of 1 (0.250 g, 0.54 mmol) in ethanol at 0° C. was treated with 2-methylpropane-1,2-diamine (0.144 g, 1.62 mmol), stirred at 0° C. for 3 h, then at room temperature for 45 minutes, heated to 40° C. for 2 h and concentrated in vacuo. The resultant residue was partitioned between ethyl acetate and water. The organic layer was separated, washed with brine, dried over sodium sulfate and concentrated. This residue was purified by flash chromatography (silica, gradient 100% hexanes to 1:9 ethyl acetate/hexanes) to afford 2 as a white solid, $^1$H NMR (300 MHz, CDCl$_3$) δ 7.73 (s, 1H), 7.56 (t, J=1.8 Hz, 1H), 7.49 (dt, J=7.7, 1.3 Hz, 1H), 7.43 (t, J=3.0 Hz, 1H), 7.40 (t, J=2.2 Hz, 1H), 7.34-7.21 (m, 4H), 3.60 (s, 2H), 1.44 (s, 3H), 1.43 (s, 3H); ESI MS m/z 484 [C$_{20}$H$_{17}$BrF$_3$N$_3$OS+H]$^+$.

Step b) Preparation of Compound 3.

A mixture of 2 (0.201 g, 0.42 mmol) and t-butyl hydroperoxide (0.75 g of a 70% solution in water, 8.30 mmol) in methanol and concentrated aqueous ammonium hydroxide (5 mL) was stirred overnight at room temperature, treated 10% aqueous sodium thiosulfate (30 mL) and concentrated to remove most of the methanol. The remaining aqueous mixture was extracted with methylene chloride. The methylene chloride extracts were combined, washed with brine, dried over sodium sulfate and concentrated. Purification of the residue by flash chromatography (silica, 97:2.5:0.5 methylene chloride/methanol/concentrated ammonium hydroxide) afforded 3 (0.134 g, 68%) as a white solid: $^1$H NMR (300 MHz, CDCl$_3$) δ 7.71 (t, J=1.7 Hz, 1H), 7.54 (d, J=8.8 Hz, 2H), 7.43-7.37 (m, 2H), 7.19-7.13 (m, 3H), 3.36 (s, 2H), 1.42 (s, 6H); ESI MS m/z 467 [C$_{20}$H$_{18}$BrF$_3$N$_4$O+H]$^+$.

Step c) Preparation of 7-[3-(2-fluoropyridin-3-yl)phenyl]-2,2-dimethyl-7-(4-trifluoromethoxyphenyl)-2,7-dihydro-3H-imidazo[1,5-a]imidazol-5-ylamine A mixture of 3 (0.134 g, 0.29 mmol), 2-fluoropyridine-3-boronic acid (0.081 g, 0.57 mmol), bis(triphenylphosphino)palladium(II) chloride (0.010 g, 0.015 mmol), triphenylphosphine (0.008 g, 0.029 mmol) and sodium carbonate (0.092 g, 0.87 mmol) in 3:1 DME/water (8.0 mL) was heated at 80° C. for 5 h, cooled to room temperature and diluted with ethyl acetate and water. The organic layer was separated, washed with brine, dried over sodium sulfate and concentrated. Purification of the resultant residue by flash chromatography (silica, 97:2.5:0.5 methylene chloride/methanol/concentrated ammonium hydroxide) afforded 0.020 g of an off-white solid. This material was freeze dried from 2:1 acetonitrile/water (6 mL) to afford the title product as a white solid, 0.0189 g (14% yield), mp 89-97° C.; $^1$H NMR (300 MHz, CDCl$_3$) δ 8.18-8.17 (m, 1H), 7.84-7.78 (m, 2H), 7.62-7.54 (m, 3H), 7.48-7.42 (m, 2H), 7.27 (m, 1H), 7.16 (d, J=8.2 Hz, 2H), 3.39 (d, J=2.2 Hz, 2H), 1.44 (s, 3H), 1.42 (s, 3H); ESI MS m/z 484 [C$_{25}$H$_{2}$,F$_4$N$_5$O$_2$+H]$^+$.

EXAMPLE 43

Preparation of 8-(2,2-Difluoro-benzo[1,3]dioxol-5-yl)-8-[3-(2-fluoro-pyridin-3-yl)phenyl]-2,3,4,8-tetrahydro-imidazo[1,5-a]pyrimidin-6-ylamine

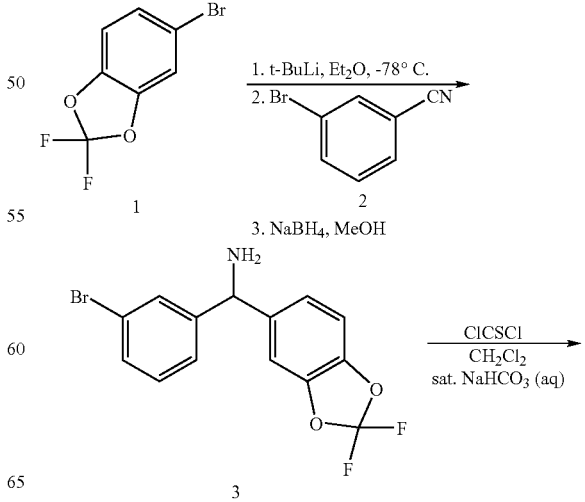

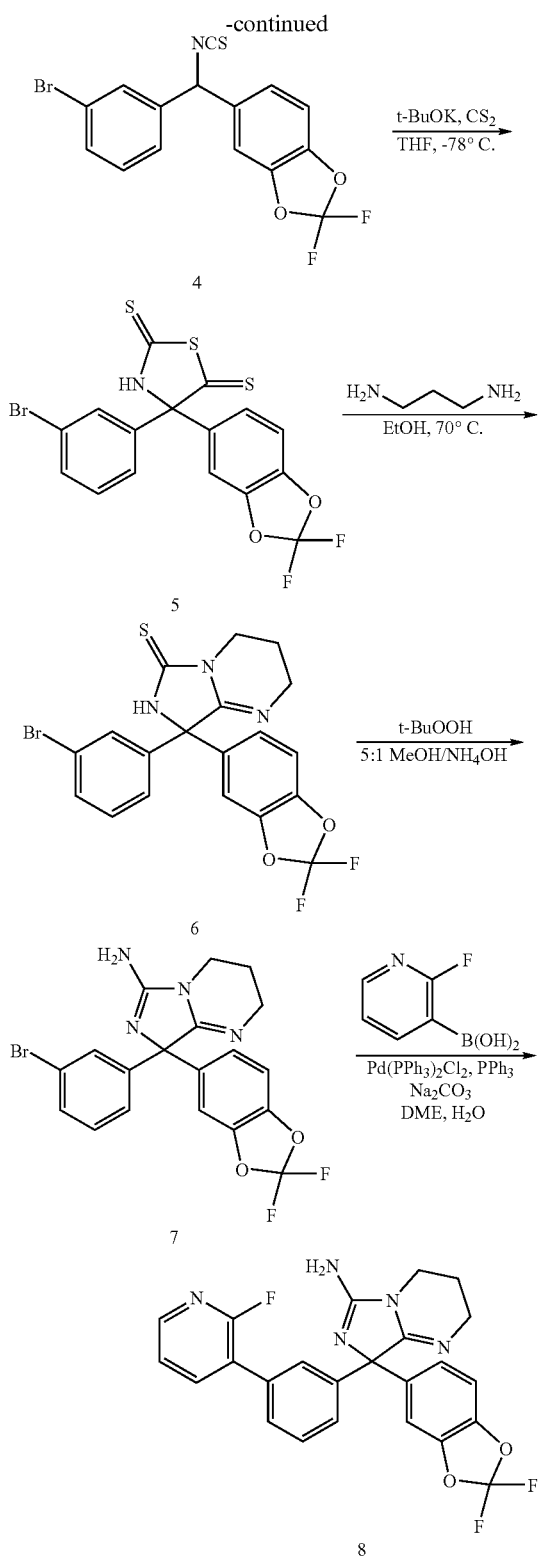

this was added 3-bromobenzonitrile (0.731 g, 4.02 mmol) in diethyl ether (20 mL) at −78° C., and the reaction mixture was stirred at −78° C. for an additional 1.5 h. The reaction was then warmed to 0° C. and methanol (60 mL) was added, followed by the portion-wise addition of sodium borohydride (0.319 g, 8.43 mmol). The cooling bath was removed and then the mixture was stirred at room temperature for 2 hr. Saturated aqueous ammonium chloride (10 mL) was added, most of the methanol and diethyl ether was removed under reduced pressure and the aqueous residue obtained was diluted with methylene chloride (200 mL) and saturated aqueous sodium bicarbonate solution (30 mL). The organic layer was separated and washed with brine, dried over sodium sulfate, filtered and concentrated. Purification by flash chromatography (silica, 9:1 hexanes/ethyl acetate) afforded 3 (0.237 g, 18%) as a colorless syrup: $^1$H NMR (300 MHz, CDCl$_3$) δ 7.54 (t, J=1.6 Hz, 1H), 7.38 (dt, J=7.8, 1.2 Hz, 1H), 7.29-7.04 (m, 4H), 6.98 (d, J=8.2 Hz, 1H), 5.17 (s, 1H); ESI MS m/z 327 [(C$_{14}$H$_{10}$BrF$_2$NO$_2$—NH$_2$)+H]$^+$.

Step b) Preparation of Compound 4

A mixture of 3 (0.416 g, 1.22 mmol) in methylene chloride and saturated aqueous sodium bicarbonate (6 mL) was cooled with an ice bath, treated with thiophosgene (0.154 g, 1.34 mmol) and stirred vigorously for 45 minutes. The organic layer was separated, washed with brine (15 mL), dried over sodium sulfate, filtered and concentrated to afford 4 (0.405 g, 87%) as a yellow syrup: $^1$H NMR (500 MHz, CDCl$_3$) δ 7.48 (dt, J=7.7, 1.6 Hz, 1H), 7.43 (t, J=6.3 Hz, 1H), 7.11-7.04 (m, 2H), 6.99 (t, J=0.6 Hz, 1H), 5.95 (s, 1H); ESI MS m/z 325 [(C$_{15}$H$_8$BrF$_2$NO$_2$S—NCS)+H]$^+$.

Step c) Preparation of Compound 5

To a mixture of potassium t-butoxide (0.130 g, 1.16 mmol) in tetrahydrofuran at −78° C. was added dropwise a solution of 4 (0.405 g, 1.05 mmol) and carbon disulfide (0.120 g, 1.58 mmol) in tetrahydrofuran, over a period of 5 min. The reaction was stirred at −78° C. for 0.5 h, then warmed to room temperature slowly and stirred overnight at room temperature. The reaction was then concentrated to remove most of the tetrahydrofuran and the residue diluted with ethyl acetate, water and brine. The organic layer was separated, washed with brine, dried over sodium sulfate, filtered and concentrated. Purification by flash chromatography (silica, 9:1 hexanes/ethyl acetate) afforded 5 (0.323 g, 67%) as a red syrup: $^1$H NMR (300 MHz, CDCl$_3$) δ 7.59-7.56 (m, 1H), 7.52-7.51 (m, 1H), 7.35-7.30 (m, 3H), 7.15 (dd, J=8.5, 1.9 Hz, 1H), 7.08 (d, J=1.5 Hz, 1H).

Step d) Preparation of Compound 6

A mixture of 5 (0.323 g, 0.702 mmol) and 1,3-diaminopropane (0.156 g, 2.11 mmol) in ethanol was heated at 70° C. for 1 h and then cooled to room temperature. The solvents were evaporated and the residue diluted with ethyl acetate, washed with water and brine, dried over sodium sulfate, filtered and concentrated. Purification by flash chromatography (silica, 4:1 hexanes/ethyl acetate) afforded 6 (0.303 g, 93%) as a white foam: $^1$H NMR (300 MHz, CDCl$_3$) δ 7.51-7.48 (m, 2H), 7.25 (d, J=1.7 Hz, 2H), 7.08-7.04 (m, 3H), 3.88 (t, J=6.0 Hz, 2H), 3.61 (t, J=1.9 Hz, 2H), 1.93-1.89 (m, 2H); ESI MS m/z 466 [C$_{19}$H$_{14}$BrF$_2$N$_3$O$_2$S+H]$^+$.

Step e) Preparation of Compound 7

A mixture of 6 (0.303 g, 0.65 mmol) and t-butyl hydroperoxide (1.18 g of a 70% solution in water, 12.9 mmol) in methanol and concentrated aqueous ammonium hydroxide (6.0 mL) was stirred overnight at room temperature. After this time, 10% aqueous sodium thiosulfate (40 mL) was added; the mixture concentrated to remove most of the methanol and then the aqueous mixture was extracted with methylene chloride. The methylene chloride extracts were combined and washed with brine, dried over sodium sulfate, filtered and concentrated. Purification by flash chromatography (silica, 97:2.5:0.5 methylene chloride/methanol/concentrated ammonium hydroxide) afforded 7 (0.208 g, 71%) as a white solid: $^1$H NMR (300 MHz, CDCl$_3$) δ 7.63 (t, J=1.8 Hz, 1H), 7.36 (dd, J=8.0, 1.9 Hz, 2H), 7.24-7.13 (m, 3H), 6.95 (dd, J=7.4, 1.7 Hz, 1H), 3.58 (t, J=5.8 Hz, 4H), 1.89-1.82 (m, 2H); ESI MS m/z 449 [$C_{19}H_{15}BrF_2N_4O_2$+H]$^+$.

Step f) Preparation of 8-(2,2-difluoro-benzo[1,3]dioxol-5-yl)-8-[3-(2-fluoropyridin-3-yl)-phenyl]-2,3,4,8-tetrahydro-imidazo[1,5-a]pyrimidin-6-ylamine A mixture of 7 (0.208 g, 0.46 mmol), 2-fluoropyridine-3-boronic acid (0.131 g, 0.93 mmol), bis(triphenylphosphino)palladium(II) chloride (0.016 g, 0.023 mmol), triphenylphosphine (0.012 g, 0.046 mmol) and sodium carbonate (0.146 g, 1.38 mmol) in 3:1 DME/water was heated at 80° C. for 2 h then stirred at room temperature overnight. The mixture was diluted with ethyl acetate and water. The organic layer was separated and washed with brine, dried over sodium sulfate, filtered and concentrated. Purification by flash chromatography (silica, 97:2.5:0.5 methylene chloride/methanol/concentrated ammonium hydroxide) afforded a colorless oil (0.180 g (84%). The oil was further purified by semi-preparative LC to afford the title product as an off-white solid, 0.045 g, mp 95-99° C.; $^1$H NMR (500 MHz, CD$_3$OD) δ 8.16-8.15 (m, 1H), 8.03-7.99 (m, 1H), 7.56 (d, J=1.5 Hz, 1H), 7.53-7.52 (m, 1H), 7.46 (t, J=7.8 Hz, 1H), 7.42-7.37 (m, 2H), 7.23-7.19 (m, 2H), 7.13 (d, J=8.3 Hz, 1H), 3.69 (t, J=5.9 Hz, 2H), 3.49 (t, J=5.8 Hz, 2H), 1.89-1.84 (m, 2H); ESI MS m/z 466 [$C_{24}H_{18}F_3N_5O_2$+H]$^+$.

EXAMPLE 44

Preparation of 8'-[4-(Difluoromethoxy)phenyl]-8'-[3-(2-fluoropyridin-3-yl)phenyl]-2',8'-dihydrospiro[cyclopropane-1,3'-imidazo[1,5-a]pyrimidin]-6'-amine

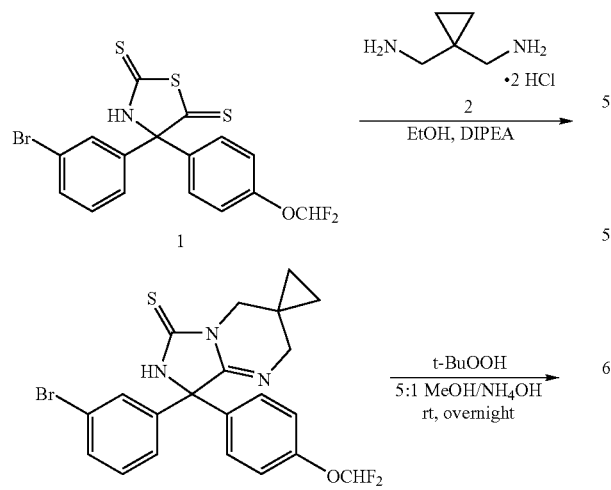

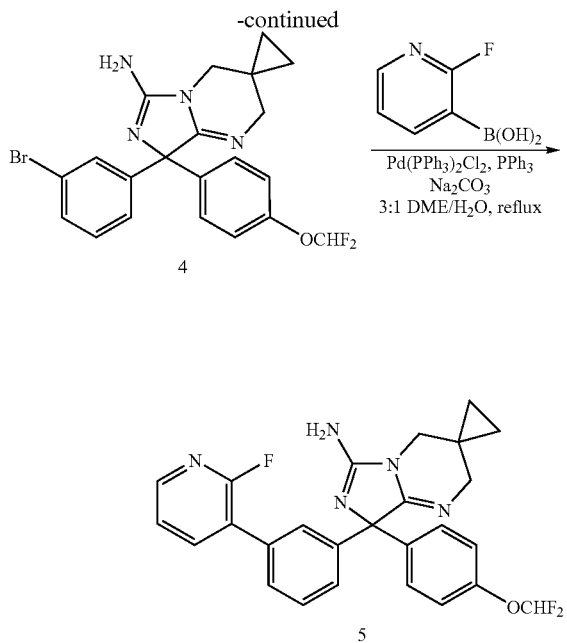

Using essentially the same procedure described in Example 42 and employing 1,1-di(aminomethyl)propane (2) as reactant, the title product was obtained as a tan solid, mp 98-108° C.; $^1$H NMR (500 MHz, CDCl$_3$) δ 8.16 (m, 1H), 7.83 (m, 1H), 7.71 (m, 1H), 7.47 (m, 4H), 7.40 (t, J=7.7 Hz, 1H), 7.24 (m, 1H), 7.05 (d, J=6.9 Hz, 2H), 6.49 (t, J=74 Hz, 1H), 3.20-3.45 (m, 4H), 0.57-0.67 (m, 4H); ESI MS m/z 478 [$C_{26}H_{22}F_3N_5O$+H]$^+$.

EXAMPLE 45

Preparation of (8R)-8-(4-Difluoromethoxy-phenyl)-8-[3-(2-fluoro-pyridin-3-yl)phenyl]-2,3,4,8-tetrahydro-imidazo[1,5-a]pyrimidin-6-ylamine [A] and (8S)-8-(4-Difluoromethoxy-phenyl)-8-[3-(2-fluoro-pyridin-3-yl)-phenyl]-2,3,4,8-tetrahydroimidazo[1,5-a]pyrimidin-6-ylamine [B]

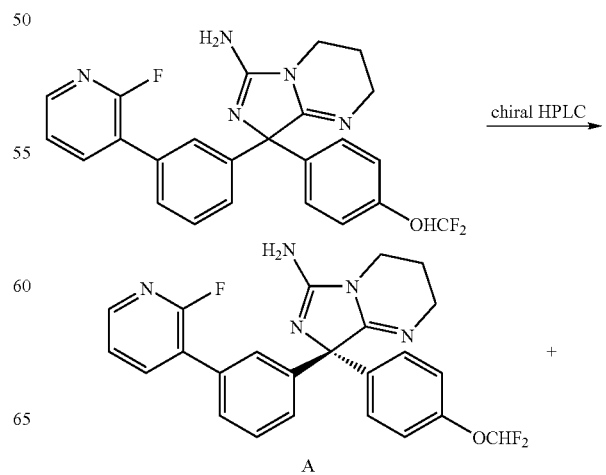

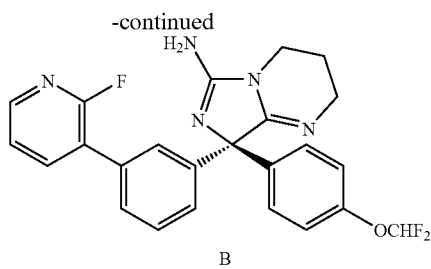

A racemic mixture of 8-(4-difluoromethoxy-phenyl)-8-[3-(2-fluoro-pyridin-3-yl)phenyl]-2,3,4,8-tetrahydro-imidazo[1,5-a]pyrimidin-6-ylamine was separated into it's enantiomers using a chiralpak AD 5×50 cm column (90:10:0.1 heptane/ethanol/diethylamine to afford the title R-isomer (A) as a white solid, mp 97-109° C.; $[\alpha]_D^{25}$ +7.8° (0.48% in MeOH); $^1$H NMR (500 MHz, CDCl$_3$) δ 8.16 (dt, J=4.8, 1.5 Hz, 1H), 7.86-7.81 (m, 1H), 7.69 (d, J=1.5 Hz, 1H), 7.52-7.46 (m, 4H), 7.40 (t, J=7.7 Hz, 1H), 7.26-7.22 (m, 1H), 7.05 (d, J=8.7 Hz, 2H), 6.48 (t, J=74.0 Hz, 1H), 3.62 (t, J=6.0 Hz, 2H), 3.60-3.56 (m, 2H), 1.87 (quintet, J=5.8 Hz, 2H); ESI MS m/z 452 [C$_{24}$H$_{20}$F$_3$N$_5$O+H]$^+$ and the title S-isomer (B) as a white solid, mp 97-110° C.; $[\alpha]_D^{25}$ -3.2° (0.47% in MeOH); $^1$H NMR (300 MHz, CDCl$_3$) δ 8.16 (m, 1H), 7.87-7.80 (m, 1H), 7.69 (br s, 1H), 7.51-7.38 (m, 5H), 7.26-7.22 (m, 1H), 7.05 (d, J=8.7 Hz, 2H), 6.48 (t, J=74.0 Hz, 1H), 3.65-3.57 (m, 4H), 1.89-1.85 (m, 2H); ESI MS m/z 452 [C$_{24}$H$_{20}$F$_3$N$_5$O+H]$^+$.

EXAMPLE 46

Preparation of 8-[4-(Difluoromethoxy)phenyl]-8-[3-(2-fluoropyridin-3-yl)phenyl]-2,8-dihydrospiro[imidazo[1,5-a]pyrimidine-3,3'-oxetan]-6-amine

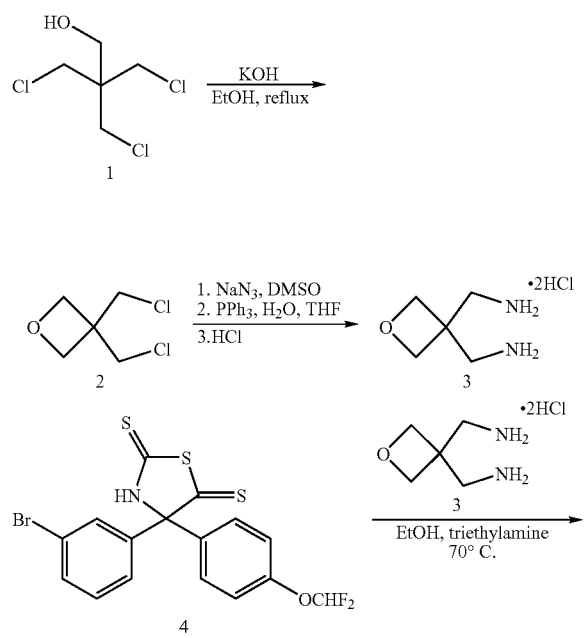

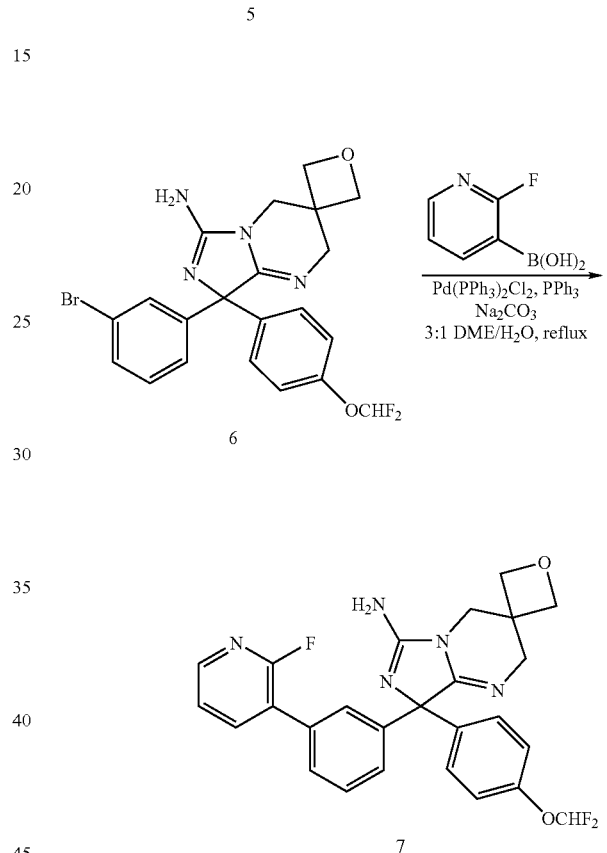

Step a) Preparation of Compound 2

A mixture of 1 (1.0 g, 5.22 mmol) and potassium hydroxide (0.345 g of 85%, 5.22 mmol) in ethanol (2 mL) was heated at reflux for 3 h. The reaction was cooled to room temperature, diluted with ethyl acetate (10 mL) and the solids that formed removed by filtration. The filtrate was concentrated to afford 2 (0.65 g, 80%) as a colorless liquid: $^1$H NMR (300 MHz, CDCl$_3$) δ 4.47 (s, 4H), 3.95 (s, 4H).

Step b) Preparation of Compound 3

A mixture of 2 (0.63 g, 4.06 mmol) and sodium azide (0.66 g, 10.2 mmol) in DMSO was heated at 65° C. overnight. The reaction was cooled to room temperature, diluted with water and extracted into methylene chloride. The combined methylene chloride extracts were washed with water, dried over sodium sulfate, filtered and concentrated at room temperature to a volume of 2 mL and diluted with THF. This solution was then treated with triphenylphospine (2.56 g, 9.75 mmol)) in THF and stirred at room temperature for 10 min, treated with water (0.29 g, 16.2 mmol) and stirred overnight at room temperature. The mixture was then concentrated, diluted with methylene chloride and extracted with 10% aqueous HCl. The combined aqueous extracts were washed with methylene chloride and concentrated to afford 3 (0.51 g, 66%) as a white solid: $^1$H NMR (500 MHz, D$_2$O) δ 4.49 (s, 4H), 3.42 (s, 4H).

Step c) Preparation of Compound 5

A mixture of 4 (0.50 g, 1.12 mmol), 3 (0.50 g, 2.64 mmol) and triethylamine (0.57 g, 5.60 mmol) in ethanol was heated at 70° C. for 3 h, cooled to room temperature, concentrated and partitioned between ethyl acetate and water. The organic layer was separated, washed with brine, dried over sodium sulfate, filtered and concentrated. Purification by flash chromatography (silica, 1:4 ethyl acetate/hexanes) afforded 5 (0.389 g, 70%) as a white foam: $^1$H NMR (500 MHz, CDCl$_3$) δ 7.61 (s, 1H), 7.49 (dt, J=7.5, 1.5 Hz, 1H), 7.47-7.44 (m, 1H), 7.33-7.19 (m, 4H), 7.11 (d, J=8.8 Hz, 2H), 6.52 (t, J=73.4 Hz, 1H), 4.52-4.47 (m, 4H), 4.14-4.06 (m, 2H), 3.87-3.77 (m, 2H); ESI MS m/z 494 [C$_{21}$H$_{18}$BrF$_2$N$_3$O$_2$S+H]$^+$.

Step c) Preparation of Compound 6

A mixture of 5 (0.389 g, 0.79 mmol) and t-butyl hydroperoxide (1.42 g of a 70% solution in water, 15.8 mmol) in methanol and concentrated aqueous ammonium hydroxide (5.0 mL) was stirred at room temperature for 7 h, treated with 10% aqueous sodium thiosulfate (30 mL) and concentrated to remove most of the methanol. The resultant aqueous mixture was extracted with methylene chloride. The methylene chloride extracts were combined and washed with brine, dried over sodium sulfate, filtered and concentrated. Purification of this residue by flash chromatography (silica, 95:5:0.25 methylene chloride/methanol/concentrated ammonium hydroxide) afforded 6 (0.179 g, 47%) as a white foam: $^1$H NMR (300 MHz, CDCl$_3$) δ 7.56 (t, J=1.7 Hz, 1H), 7.40-7.37 (m, 1H), 7.38 (d, J=8.8 Hz, 2H), 7.29-7.26 (m, 1H), 7.15 (t, J=7.9 Hz, 1H), 7.04 (d, J=8.7 Hz, 2H), 6.48 (t, J=73.9 Hz, 1H), 4.57-4.53 (m, 2H), 4.46-4.42 (m, 2H), 3.79 (s, 4H); ESI MS m/z 477 [C$_{21}$H$_{19}$BrF$_2$N$_4$O$_2$+H]$^+$.

Step d) Preparation of of 8-[4-(difluoromethoxy)phenyl]-8-[3-(2-fluoropyridin-3-yl)phenyl]-2,8-dihydrospiro[imidazo[1,5-a]pyrimidine-3,3'-oxetan]-6-amine A mixture of 6 (0.10 g, 0.21 mmol), 2-fluoropyridine-3-boronic acid (0.035 g, 0.250 mmol), bis(triphenylphosphino)palladium(II) chloride (0.0073 g, 0.11 mmol), triphenylphosphine (0.0055 g, 0.021 mmol) and sodium carbonate (0.066 g, 0.63 mmol) in 3:1 DME/water was heated at reflux temperature for 2 h, cooled to room temperature and diluted with ethyl acetate and water. The organic layer was separated and washed with brine, dried over sodium sulfate, filtered and concentrated. Purification of this residue by flash chromatography (silica, 97:2.5:0.5 methylene chloride/methanol/concentrated ammonium hydroxide) afforded a yellow foam (0.089 g, 85%). This foam was further purified by semipreparative LC to afford the title product as a white solid; mp 96-107° C.; $^1$H NMR (500 MHz, CD$_3$OD) δ8.17-8.16 (m, 1H), 8.02-7.98 (m, 1H), 7.52-7.51 (m, 2H), 7.45 (t, J=7.9 Hz, 1H), 7.40-7.34 (m, 4H), 7.09 (d, J=8.8 Hz, 2H), 6.01 (t, J=74.1 Hz, 1H), 4.50-4.47 (m, 4H), 3.97-3.89 (m, 2H), 3.76-3.69 (m, 2H); ESI MS m/z 496 [C$_{26}$H$_{22}$F$_3$N$_5$O$_2$+H]$^+$;

EXAMPLE 47

Preparation of 8'-[4-(difluoromethoxy)phenyl]-8'-[3-(2-fluoropyridin-3-yl)phenyl]-2',8'-dihydrospiro[cyclobutane-1,3'-imidazo[1,5-a]pyrimidin]-6'-amine

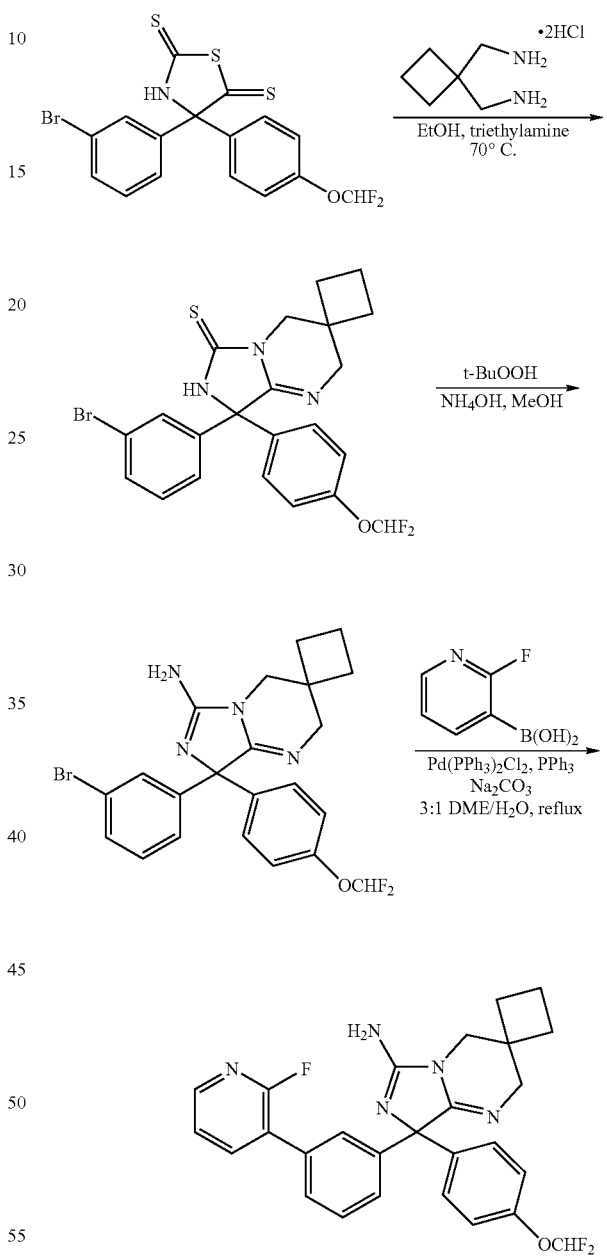

Using essentially the same procedure described in Example 44 and employing 1,1-di(aminomethylcyclobutane as starting reactant, the title product was obtained as a white solid, mp 220-226° C.; $^1$H NMR (500 MHz, CD$_3$OD) δ8.16-8.15 (m, 1H), 8.01-7.97 (m, 1H), 7.54-7.51 (m, 2H), 7.44 (t, J=7.8 Hz, 1H), 7.40-7.37 (m, 4H), 7.08 (d, J=8.8 Hz, 2H), 6.80 (t, J=74.1 Hz, 1H), 3.65-3.58 (m, 2H), 3.46-3.39 (m, 2H), 2.09-2.01 (m, 2H), 1.92-1.87 (m, 4H); ESI MS m/z 492 [C$_{27}$H$_{24}$F$_3$N$_5$O+H]$^+$.

EXAMPLE 48

Evaluation of the Enzyme Activity of Test Compounds and the Inhibition of hBACE1, MuBACE1 and hBACE2 by Test Compounds Assay Conditions: 10 nM human BACE1 (or 10 nM Murine BACE1, 1.5 nM human BACE2) 25 µM substrate (WABC-6, MW 1549.6, from AnaSpec); final buffer conditions: 50 mM Na-Acetate, pH 4.5, 0.05% CHAPS, 25% PBS; temperature: room temperature; reagent information: Na-Acetate: Aldrich, Cat.# 24,124-5 CHAPS: Research Organics, Cat. # 1304C 1×PBS: Mediatech (Cellgro), Cat# 21-031-CV; peptide substrate AbzSEVNLDAEFRDpa: AnaSpec, Peptide Name: WABC-6; determination of stock substrate (AbzSEVNLDAEFRDpa) concentration: a 25 mM stock solution in dimethyl sulfoxide (DMSO) is prepared using the peptide weight and MW and diluted to 25 µM. The concentration is determined by absorbance at 354 nm using an extinction coefficient E of 18172 $M^{-1}cm^{-1}$, The substrate stock is stored in small aliquots at −80° C. [Substrate Stock]=$ABS^{354\ nm}*10^6/18172$ (in mM)

Determination of Stock Enzyme Concentration: The stock concentration of each enzyme by ABS at 280 nm using □ of 64150 $M^{-1}cm^{-1}$ for hBACE1 and MuBACE1, 62870 $M^{-1}cm^{-1}$ for hBACE2 in 6 M Guanidinium Hydrochloride (from Research Organics, Cat. # 5134G-2), pH 6.

(The extinction coefficient $\epsilon^{280\ nm}$ for each enzyme was calculated based on known amino acid composition and published extinction coefficients for Trp (5.69 $M^{-1}cm^{-1}$) and Tyr (1.28 $M^{-1}cm^{-1}$) residues (*Anal. Biochem.* 182, 319-326).

Dilution and mixing steps: total reaction volume: 100 µL
1. 2× inhibitor dilutions in buffer A (66.7 mM Na-Acetate, pH 4.5, 0.0667% CHAPS) are prepared,
2. 4× enzyme dilution in buffer A (66.7 mM Na-Acetate, pH 4.5, 0.0667% CHAPS) are prepared,
3. 100 µM substrate dilution in 1×PBS is prepared,
4. 50 µL 2× Inhibitor and 25 µL 100 µM substrate are added to each well of 96-well plate (from DYNEX Technologies, VWR #: 11311-046), the immediately 25 µL 4× enzyme are added to the inhibitor and substrate mixer, the fluorescence readings are initiated.

Fluorescence Readings: Readings at $\lambda_{ex}$ 320 nm and $\lambda_{em}$ 420 nm are taken every 40-sec for 30 min at room temperature to determine the linear slope for substrate cleavage rate ($v_i$).

Calculation of % Inhibition: % Inhibition=$100*(1-v_i/v_0)$ ($v_i$=substrate cleavage rate in the presence of inhibitor, $v_0$=substrate cleavage rate in the absence of inhibitor)

$IC_{50}$ Determination: % Inhibition=$[(B*IC_{50}{}^n)+(100*I_0{}^n)]/(IC_{50}{}^n+I_0{}^n)$, Fluorescent Kinetic Assay for Human Recombinant BACE 2

This assay is used to provide kinetic and selectivity parameters for the analyses of the tested compounds.

Materials and methods: final assay conditions: 10 nM human BACE1 (or 10 nM Murine BACE1, 1.5 nM human BACE2) 25 µM Substrate (WABC-6, MW 1549.6, from AnaSpec). Final buffer conditions: 50 mM Na-Acetate, pH 4.5, 0.05% CHAPS, 25% PBS. Temperature: room temperature. Reagent Information: Na-Acetate: Aldrich, Cat.# 24,124-5 CHAPS: Research Organics, Cat. # 1304$C_1$×PBS: Mediatech (Cellgro), Cat# 21-031-CV Peptide Substrate AbzSEVNLDAEFRDpa: AnaSpec, Peptide Name: WABC-6

Determination of stock substrate (AbzSEVNLDAEFRDpa) concentration: A 25 mM stock solution in DMSO is prepared using the peptide weight and MW, and diluted to 25 µM. The concentration is determined by absorbance at 354 nm using an extinction coefficient E of 18172 $M^{-1}cm^{-1}$. The substrate stock is stored in small aliquots at −80° C. [Substrate Stock]=$ABS^{354\ nm}*10^6/18172$ (in mM)

Determination of stock enzyme concentration: The stock concentration of each enzyme is determined by ABS at 280 nm using $\epsilon$ of 64150 $M^1cm^1$ for hBACE1 and MuBACE1, 62870 $M^{-1}cm^{-1}$ for hBACE2 in 6 M guanidinium hydrochloride (from Research Organics, Cat. # 5134G-2), pH 6. (The extinction coefficient $\epsilon^{280\ nm}$ for each enzyme is calculated based on known amino acid composition and published extinction coefficients for Trp (5.69 $M^{-1}cm^{-1}$) and Tyr (1.28 $M^{-1}cm^{-1}$) residues (*Anal. Biochem.* 182, 319-326).)

Dilution and Mixing Steps: Total Reaction Voume.: 100 µL
1. 2× inhibitor dilutions in buffer A (66.7 mM Na-Acetate, pH 4.5, 0.0667% CHAPS) are prepared,
2. 4× enzyme dilution in buffer A (66.7 mM Na-Acetate, pH 4.5, 0.0667% CHAPS) are prepared,
3. 100 µM substrate dilution in 1×PBS, 50 mL 2× Inhibitor and 25/L 100 µM substrate are added to each well of 96-well plate (from DYNEX Technologies, VWR #: 11311-046), then immediately 25 µL 4× enzyme is added to the inhibitor and substrate mixer and the fluorescence readings are initiated.

Fluorescence Readings: Readings at $\lambda_{ex}$ 320 nm, $\lambda_{em}$ 420 nm are taken every 40-sec for 30 min at room temperature and to determine the linear slope for substrate cleavage rate ($v_i$).

Analysis of calculation of % inhibition: % Inhibition=$100*(1-v_i/v_0)$ $v_i$=substrate cleavage rate in the presence of inhibitor, $v_0$=substrate cleavage rate in the absence of inhibitor)
$IC_{50}$ Determination:

% Inhibition=$((B*IC_{50}{}^n)+(100*I_0{}^n))/(IC_{50}{}^n+I_0{}^n)$,

The data obtained are shown in Table II below. Unless otherwise noted, the $IC_{50}$ value represents the value obtained at 100% inhibition.

TABLE II

| Ex. | $IC_{50}$ (µM) | |
|---|---|---|
| No. | BACE1 | BACE2 |
| 5 | 0.23 | 25 (50% inhibition) |
| 13 | 0.15 | 25 (25% inhibition) |
| 14 | 0.14 | 25 (65% inhibition) |
| 15 | 0.10 | 25 (44% inhibition) |
| 16 | 0.11 | 25 (49% inhibition) |
| 17 | 0.06 | 11.39 |
| 18 | 0.06 | 25 (62% inhibition) |
| 19 | 0.08 | 3.22 |
| 20 | 0.04 | 0.54 |
| 21 | 0.09 | 6.57 |
| 22 | 0.12 | 25 (60% inhibition) |
| 23 | 0.12 | 25 (42% inhibition) |
| 24 | 0.06 | 8.18 |
| 25 | 0.083 | 9.867 |
| 26 | 0.04 | 1.66 |
| 27 | 0.10 | 4.44 |
| 28 | 0.06 | 4.68 |
| 30A | 0.37 | 25 (35% inhibition) |
| 30B | 0.02 | 3.79 |
| 31A | 0.03 | 10.37 |
| 31B | 0.79 | 25 (28% inhibition) |
| 32A | 0.029 | 0.272 |
| 32B | 19% at 5 uM | 34% at 25 µM |
| 33A | 0.05 | 4.00 |

TABLE II-continued

| Ex. No. | IC$_{50}$ (µM) BACE1 | BACE2 |
|---|---|---|
| 33B | 43% at 5 µM | 25% at 25 µM |
| 34 | 0.979 | 25% at 25 µM |
| 35 | 0.072 | 12.252 |
| 36 | 0.071 | 7.319 |
| 37 | 0.152 | 10.803 |
| 38 | 0.093 | 47% at 15.5 µM |
| 39 | 0.194 | 10.532 |
| 40 | 0.160 | 4.374 |
| 41 | 0.018 | 1.234 |
| 42 | 0.15 | 52% at 25 µM |
| 43 | 0.74 | 53% at 25 µM |
| 44 | 0.02 | 2.26 |
| 45A | 0.01 | 0.70 |
| 45B | 49% at 2.5 uM | 60% at 25 µM |
| 46 | 0.01 | 0.55 |
| 47 | 0.01 | 1.15 |

Results and Discussion:

As can be seen from the data shown on Table II hereinabove, the compounds of the invention are potent and selective inhibitors of BACE1.

What is claimed is:

1. A compound of formula I

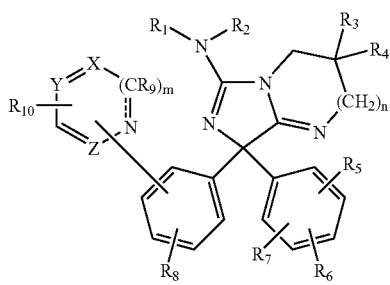

(I)

wherein X is N, NO or CR$_{19}$;
Y is N, NO or CR$_{11}$;
Z is N, NO or CR$_{20}$ with the proviso that no more than two of X, Y or Z may be N or NO;
R$_1$ and R$_2$ are each independently H, CN or an optionally substituted C$_1$-C$_4$alkyl group;
R$_3$ and R$_4$ are each independently H, or an optionally substituted C$_1$-C$_4$ alkyl group or R$_3$ and R$_4$ may be taken together to form a 3- to 7-membered ring optionally containing one or two heteroatoms selected from O, N or S or R$_3$ may be taken together with the atom to which it is attached and an adjacent carbon atom to form a double bond;
R$_5$ and R$_6$ are each independently H, halogen, NO$_2$, CN, OR$_{13}$, NR$_{14}$R$_{15}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted or when attached to adjacent carbon atoms R$_5$ and R$_6$ may be taken together with the atoms to which they are attached to form an optionally substituted 5- to 7-membered ring optionally containing one or two heteroatoms selected from O, N or S;
R$_7$, R$_8$, R$_9$, R$_{10}$, R$_{11}$, R$_{19}$ and R$_{20}$ are each independently H, halogen, NO$_2$, CN, OR$_{16}$, NR$_{17}$R$_{18}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted;

m is 0 or 1;
n is 1;
------ is a single bond or a double bond with the proviso that when m is 0 then ------ must be a single bond;
R$_{13}$ and R$_{16}$ are each independently H or a C$_1$-C$_6$alkyl, C$_1$-C$_6$haloalkyl, C$_2$-C$_6$alkenyl, C$_2$-C$_6$alkynyl, C$_3$-C$_8$cycloalkyl or aryl group each optionally substituted; and
R$_{14}$, R$_{15}$, R$_{17}$ and R$_{18}$ are each independently H or C$_1$-C$_4$alkyl; or
a tautomer thereof, a stereoisomer thereof or a pharmaceutically acceptable salt thereof.

2. The compound according to claim 1 wherein R$_1$ and R$_2$ are H.

3. The compound according to claim 1 wherein m and n are 1.

4. The compound according to claim 1 having the structure Ia

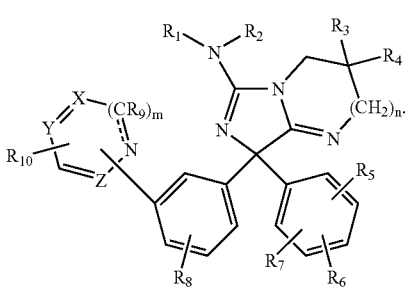

(Ia)

5. The compound according to claim 4 having the structure Ib

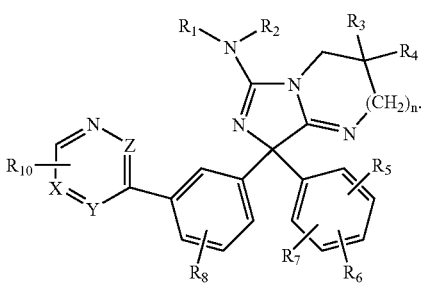

(Ib)

6. The compound according to claim 5 wherein R$_1$ and R$_2$ are H.

7. The compound according to claim 6 wherein X is N.

8. The compound according to claim 1 selected from the group consisting of:
8-(3-pyrimidin-5-ylphenyl)-8-[4-(trifluoromethoxy)phenyl]-2,3,4,8-tetrahydroimidazo[1,5-a]pyrimidin-6-amine;
8-[4-fluoro-3-(4-fluoropyridin-3-yl)phenyl]-8-[4-(trifluoromethoxy)phenyl]-2,3,4,8-tetrahydroimidazo[1,5-a]pyrimidin-6-amine;
8-[3-(5-fluoropyridin-3-yl)phenyl]-8-[4-(trifluoromethoxy)phenyl]-2,3,4,8-tetrahydroimidazo[1,5-a]pyrimidin-6-amine;
8-[3-(5-chloropyridin-3-yl)phenyl]-8-[4-(trifluoromethoxy)phenyl]-2,3,4,8-tetrahydroimidazo[1,5-a]pyrimidin-6-amine;

(8S)-8-[3-(2-fluoropyridin-3-yl)phenyl]-8-[4-(trifluoromethoxy)phenyl]-2,3,4,8-tetrahydroimidazo[1,5-a]pyrimidin-6-amine;

(8R)-8-[3-(2-fluoropyridin-3-yl)phenyl]-8-[4-(trifluoromethoxy)phenyl]-2,3,4,8-tetrahydroimidazo[1,5-a]pyrimidin-6-amine;

(8R)-8-(3-pyrimidin-5-ylphenyl)-8-[4-(trifluoromethoxy)phenyl]-2,3,4,8-tetrahydroimidazo[1,5-a]pyrimidin-6-amine;

(8S)-8-(3-pyrimidin-5-ylphenyl)-8-[4-(trifluoromethoxy)phenyl]-2,3,4,8-tetrahydroimidazo[1,5-a]pyrimidin-6-amine;

8-[3-(4-fluoropyridin-3-yl)phenyl]-8-[4-(trifluoromethoxy)phenyl]-2,3,4,8-tetrahydroimidazo[1,5-a]pyrimidin-6-amine;

8-[3-(2-fluoropyridin-3-yl)phenyl]-8-(4-methoxyphenyl)-2,3,4,8-tetrahydroimidazo[1,5-a]pyrimidin-6-amine;

8-(4-methoxyphenyl)-8-(3-pyrimidin-5-ylphenyl)-2,3,4,8-tetrahydroimidazo[1,5-a]pyrimidin-6-amine;

8-(4-fluoro-3-pyrimidin-5-ylphenyl)-8-(4-methoxyphenyl)-2,3,4,8-tetrahydroimidazo[1,5-a]pyrimidin-6-amine;

8-[4-fluoro-3-(2-fluoropyridin-3-yl)phenyl]-8-(4-methoxyphenyl)-2,3,4,8-tetrahydroimidazo[1,5-a]pyrimidin-6-amine;

8-(4-fluoro-3-pyrimidin-5-ylphenyl)-8-[4-(trifluoromethoxy)phenyl]-2,3,4,8-tetrahydroimidazo[1,5-a]pyrimidin-6-amine;

8-[3-(2-fluoropyridin-3-yl)phenyl]-8-[4-(trifluoromethoxy)phenyl]-2,3,4,8-tetrahydroimidazo[1,5-a]pyrimidin-6-amine;

8-[4-fluoro-3-(5-fluoropyridin-3-yl)phenyl]-8-[4-(trifluoromethoxy)phenyl]-2,3,4,8-tetrahydroimidazo[1,5-a]pyrimidin-6-amine;

8-[4-fluoro-3-(2-fluoropyridin-3-yl)phenyl]-8-[4-(trifluoromethoxy)phenyl]-2,3,4,8-tetrahydroimidazo[1,5-a]pyrimidin-6-amine;

a tautomer thereof;
a stereoisomer thereof; and
a pharmaceutically acceptable salt thereof.

9. A method for the treatment, or amelioration of Alzheimer's in patient which comprises providing said patient with therapeutically effective amount of compound of formula I

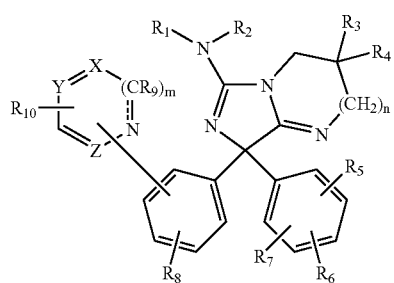

(I)

wherein X is N, NO or $CR_{19}$;
Y is N, NO or $CR_{11}$;
Z is N, NO or $CR_{20}$ with the proviso that no more than two of X, Y or Z may be N or NO;
$R_1$ and $R_2$ are each independently H, CN or an optionally substituted $C_1$-$C_4$ alkyl group;
$R_3$ and $R_4$ are each independently H, or an optionally substituted $C_1$-$C_4$ alkyl group or $R_3$ and $R_4$ may be taken together to form a 3- to 7-membered ring optionally containing one or two heteroatoms selected from O, N or S or $R_3$ may be taken together with the atom to which it is attached and an adjacent carbon atom to form a double bond;

$R_5$ and $R_6$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_5$ and $R_6$ may be taken together with the atoms to which they are attached to form an optionally substituted 5- to 7-membered ring optionally containing one or two heteroatoms selected from O, N or S;

$R_7$, $R_8$, $R_9$, $R_{10}$, $R_{11}$, $R_{19}$ and $R_{20}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

m is 0 or 1;
n is 1;
------ is a single bond or a double bond with the proviso that when m is 0 then ------ must be a single bond;

$R_{13}$ and $R_{16}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and $R_{14}$, $R_{15}$, $R_{17}$ and $R_{18}$ are each independently H or $C_1$-$C_4$alkyl; or a tautomer thereof, a stereoisomer thereof or a pharmaceutically acceptable salt thereof.

10. The method according to claim 9 having a formula I compound wherein the structure is Ia

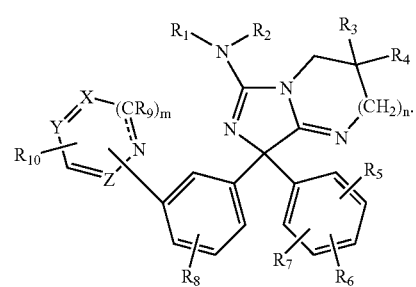

(Ia)

11. The method according to claim 10 having a formula I compound wherein the structure is Ib

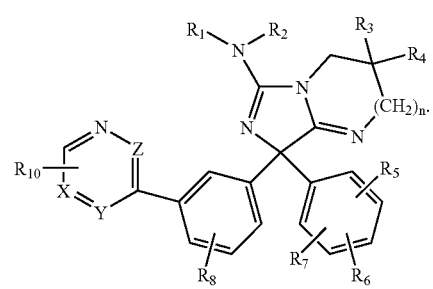

(Ib)

12. A pharmaceutical composition which comprises a pharmaceutically acceptable carrier and an effective amount of a compound of formula I

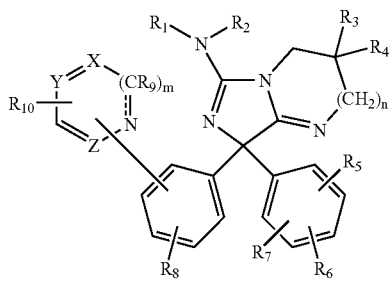

(I)

wherein X is N, NO or CR$_{19}$;
Y is N, NO or CR$_{11}$;
Z is N, NO or CR$_{20}$ with the proviso that no more than two of X, Y or Z may be N or NO;
R$_1$ and R$_2$ are each independently H, CN or an optionally substituted C$_1$-C$_4$alkyl group;
R$_3$ and R$_4$ are each independently H, or an optionally substituted C$_1$-C$_4$ alkyl group or R$_3$ and R$_4$ may be taken together to form a 3- to 7-membered ring optionally containing one or two heteroatoms selected from O, N or S or R$_3$ may be taken together with the atom to which it is attached and an adjacent carbon atom to form a double bond;
R$_5$ and R$_6$ are each independently H, halogen, NO$_2$, CN, OR$_{13}$, NR$_{14}$R$_{15}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted or when attached to adjacent carbon atoms R$_5$ and R$_6$ may be taken together with the atoms to which they are attached to form an optionally substituted 5- to 7-membered ring optionally containing one or two heteroatoms selected from O, N or S;
R$_7$, R$_8$, R$_9$, R$_{10}$, R$_{11}$, R$_{19}$ and R$_{20}$ are each independently H, halogen, NO$_2$, CN, OR$_{16}$, NR$_{17}$R$_{18}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted;
m is 0 or 1;
n is 1;
------ is a single bond or a double bond with the proviso that when m is 0 then ------ must be a single bond;
R$_{13}$ and R$_{16}$ are each independently H or a C$_1$-C$_6$alkyl, C$_1$-C$_6$haloalkyl, C$_2$-C$_6$alkenyl, C$_2$-C$_6$alkynyl, C$_3$-C$_8$cycloalkyl or aryl group each optionally substituted; and
R$_{14}$, R$_{15}$, R$_{17}$ and R$_{18}$ are each independently H or C$_1$-C$_4$alkyl; or
a tautomer thereof, a stereoisomer thereof or a pharmaceutically acceptable salt thereof.

13. The composition according to claim 12 having a formula I compound wherein the structure is Ia

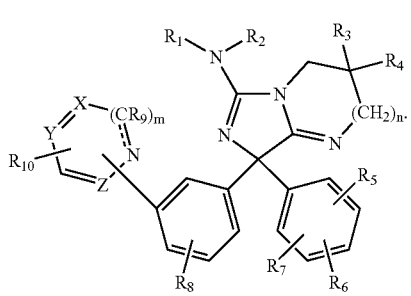

(Ia)

14. The composition according to claim 13 having a formula I compound wherein the structure is Ib

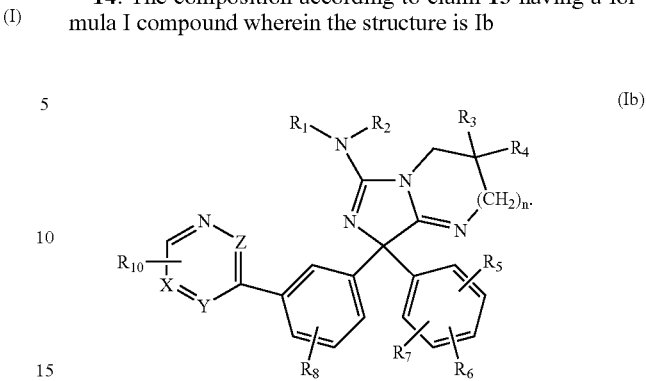

(Ib)

15. The composition according to claim 14 wherein R$_1$ and R$_2$ are H and Y is CR$_{11}$.

16. The composition according to claim 12 having a formula I compound selected from the group consisting of:
8-(3-pyrimidin-5-ylphenyl)-8-[4-(trifluoromethoxy)phenyl]-2,3,4,8-tetrahydroimidazo[1,5-a]pyrimidin-6-amine;
8-[4-fluoro-3-(4-fluoropyridin-3-yl)phenyl]-8-[4-(trifluoromethoxy)phenyl]-2,3,4,8-tetrahydroimidazo[1,5-a]pyrimidin-6-amine;
8-[3-(5-fluoropyridin-3-yl)phenyl]-8-[4-(trifluoromethoxy)phenyl]-2,3,4,8-tetrahydroimidazo[1,5-a]pyrimidin-6-amine;
8-[3-(5-chloropyridin-3-yl)phenyl]-8-[4-(trifluoromethoxy)phenyl]-2,3,4,8-tetrahydroimidazo[1,5-a]pyrimidin-6-amine;
(8S)-8-[3-(2-fluoropyridin-3-yl)phenyl]-8-[4-(trifluoromethoxy)phenyl]-2,3,4,8-tetrahydroimidazo[1,5-a]pyrimidin-6-amine;
(8R)-8-[3-(2-fluoropyridin-3-yl)phenyl]-8-[4-(trifluoromethoxy)phenyl]-2,3,4,8-tetrahydroimidazo[1,5-a]pyrimidin-6-amine;
(8R)-8-(3-pyrimidin-5-ylphenyl)-8-[4-(trifluoromethoxy)phenyl]-2,3,4,8-tetrahydroimidazo[1,5-a]pyrimidin-6-amine;
(8S)-8-(3-pyrimidin-5-ylphenyl)-8-[4-(trifluoromethoxy)phenyl]-2,3,4,8-tetrahydroimidazo[1,5-a]pyrimidin-6-amine;
8-[3-(4-fluoropyridin-3-yl)phenyl]-8-[4-(trifluoromethoxy)phenyl]-2,3,4,8-tetrahydroimidazo[1,5-a]pyrimidin-6-amine;
8-[3-(2-fluoropyridin-3-yl)phenyl]-8-(4-methoxyphenyl]-2,3,4,8-tetrahydroimidazo[1,5-a]pyrimidin-6-amine;
8-(4-methoxyphenyl)-8-(3-pyrimidin-5-ylphenyl)-2,3,4,8-tetrahydroimidazo[1,5-a]pyrimidin-6-amine;
8-(4-fluoro-3-pyrimidin-5-ylphenyl)-8-(4-methoxyphenyl)-2,3,4,8-tetrahydroimidazo[1,5-a]pyrimidin-6-amine;
8-[4-fluoro-3-(2-fluoropyridin-3-yl)phenyl]-8-(4-methoxyphenyl)-2,3,4,8-tetrahydroimidazo[1,5-a]pyrimidin-6-amine;
8-(4-fluoro-3-pyrimidin-5-ylphenyl)-8-[4-(trifluoromethoxy)phenyl]-2,3,4,8-tetrahydroimidazo[1,5-a]pyrimidin-6-amine;
8-[3-(2-fluoropyridin-3-yl)phenyl]-8-[4-(trifluoromethoxy)phenyl]-2,3,4,8-tetrahydroimidazo[1,5-a]pyrimidin-6-amine;

8-[4-fluoro-3-(5-fluoropyridin-3-yl)phenyl]-8-[4-(trifluoromethoxy)phenyl]-2,3,4,8-tetrahydroimidazo[1,5-a]pyrimidin-6-amine;

8-[4-fluoro-3-(2-fluoropyridin-3-yl)phenyl]-8-[4-(trifluoromethoxy)phenyl]-2,3,4,8-tetrahydroimidazo[1,5-a]pyrimidin-6-amine;

a tautomer thereof;
a stereoisomer thereof; and
a pharmaceutically acceptable salt thereof.

17. A process for the preparation of a compound of formula I

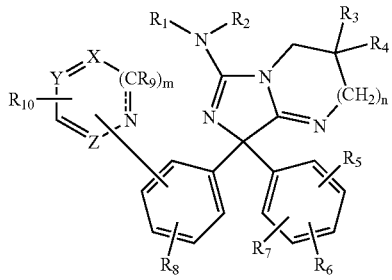

(I)

wherein X is N, NO or $CR_{19}$;

Y is N, NO or $CR_{11}$;

Z is N, NO or $CR_{20}$ with the proviso that no more than two of X, Y or Z may be N or NO;

$R_1$ and $R_2$ are each independently H, CN or an optionally substituted $C_1$-$C_4$alkyl group;

$R_3$ and $R_4$ are each independently H, or an optionally substituted $C_1$-$C_4$ alkyl group or $R_3$ and $R_4$ may be taken together to form a 3- to 7-membered ring optionally containing one or two heteroatoms selected from O, N or S or $R_3$ may be taken together with the atom to which it is attached and an adjacent carbon atom to form a double bond;

$R_5$ and $R_6$ are each independently H, halogen, $NO_2$, CN, $OR_{13}$, $NR_{14}R_{15}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted or when attached to adjacent carbon atoms $R_5$ and $R_6$ may be taken together with the atoms to which they are attached to form an optionally substituted 5- to 7-membered ring optionally containing one or two heteroatoms selected from O, N or S;

$R_7$, $R_8$, $R_9$, $R_{10}$, $R_{11}$, $R_{19}$ and $R_{20}$ are each independently H, halogen, $NO_2$, CN, $OR_{16}$, $NR_{17}R_{18}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

m is 0 or 1;

n is 1;

------ is a single bond or a double bond with the proviso that when m is 0 then ------ must be a single bond;

$R_{13}$ and $R_{16}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and $R_{14}$, $R_{15}$, $R_{17}$ and $R_{18}$ are each independently H or $C_1$-$C_4$alkyl;

which process comprises reacting a compound of formula II

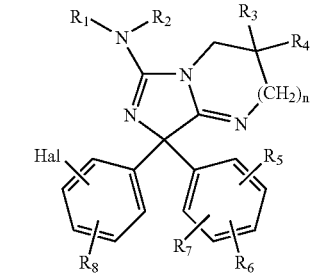

(II)

wherein Hal is Cl or Br and $R_1$, $R_2$, $R_4$, $R_5$, $R_6$, $R_7$, $R_8$, and n are as described for formula I hereinabove with a compound of formula III

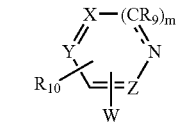

(III)

wherein W is $B(OH)_2$, $Sn(n-Bu)_3$ or $Sn(CH_3)_3$ and X, Y, Z, $R_9$, $R_{10}$ and m are as described for formula I hereinabove in the presence of a palladium catalyst optionally in the presence of a solvent.

* * * * *